United States Patent [19]

Yu et al.

[11] Patent Number: 5,641,760
[45] Date of Patent: Jun. 24, 1997

[54] METHOD OF TREATING CANDIDA INFECTION

[75] Inventors: Lei Yu; Kok Kheong Lee; Hasmukh B. Sheth, all of Edmonton; Randall T. Irvin, Sherwood Park; Robert S. Hodges, Edmonton, all of Canada

[73] Assignee: Pence, Inc., Canada

[21] Appl. No.: 261,487

[22] Filed: Jun. 17, 1994

[51] Int. Cl.$^6$ .................................................. A61K 31/715
[52] U.S. Cl. .................................. 514/53; 514/2; 514/23; 536/123.13
[58] Field of Search ........................... 514/2, 23, 25, 514/53; 536/123.13

[56] References Cited

U.S. PATENT DOCUMENTS

| | | | |
|---|---|---|---|
| 4,725,576 | 2/1988 | Pollock et al. | 514/2 |
| 5,118,705 | 6/1992 | Trani et al. | 514/455 |
| 5,238,843 | 8/1993 | Carpenter et al. | 435/264 |
| 5,242,800 | 9/1993 | Jimenez et al. | 435/7.2 |
| 5,258,304 | 11/1993 | Carpenter et al. | 435/264 |
| 5,356,803 | 10/1994 | Carpenter et al. | 435/200 |
| 5,395,541 | 3/1995 | Carpenter et al. | 252/174.12 |

*Primary Examiner*—John Kight
*Assistant Examiner*—Howard C. Lee
*Attorney, Agent, or Firm*—Carol A. Stratford; Peter J. Dehlinger

[57] ABSTRACT

A method of treating *Candida albicans* infection is disclosed. In one embodiment, for treatment of oral or vaginal infection, the treatment is by topical application of a composition of conjugates that are each composed of a carrier structure and multiple βGalNac(1-4)βGal moieties attached to the structure. In another embodiment, for treatment of systemic infection, the treatment is by parenteral administration of a humanized form of a mouse monoclonal antibody produced by mouse hybridoma cell line Fm16 or cell line PK99H.

8 Claims, 17 Drawing Sheets

METHOD OF TREATING CANDIDA INFECTION

1. FIELD OF THE INVENTION

The present invention relates to a treatment method for Candida yeast infection, particularly infection by *C. albicans*.

2. REFERENCES

Arakatsu et al., *J. Immunol.* 97:858 (1966).
Ausubel, F. M. et al. *Current Protocols in Molecular Biology*, John Wiley and Sons, Media, PA.
Clackson, T. et al., 1991, *Nature* 352: 624–628 Co, M. S., et al., 1992, *J. Immunol.* 148: 1129.
Cox, F., J. Lab. Clin. Med., 102:960 (1983).
Dubois, M., et al. Anal Chem, 28:350 (1956).
Gardiner, R. B., et al., Exp. Mycol., 9:334 (1985).
Hakimi, J., et al., 1993, *J. Immunology* 151: 1075–1085.
Huse, W. D., et al., 1992, *Biotechnology* 24: 517–23.
Huse, W. D., et al., 1989, *Science* 246: 1275–81.
Jones, S. T. and Bendig, M. M., 1991, *Bio/Technology* 9: 88.
Kettleborough, C. A., 1991, *Protein Engng* 4: 773–783.
Lemieux et al., U.S. Pat. No. 4,137,401 (1979).
Mishell, B. B. and Shiigi, S. M., editors (1980) *Selected Methods in Cellular Immunology*, W. H. Freeman and Co., San Francisco.
Nieto, A., et al., Mol. Immunol. 21:537–543 (1984).
Ogura, H., et al., *Carbohydrates: Synthetic Methods and Applications in Medicinal Chemistry*, Kodansha Ltd., Tokyo, 1992.
Pinto et al. *Carb. Res.* 124:313–318 (1983).
Queen, C., et al., 1989, *Proc. Natl. Acad. Sci. USA* 86: 10029.
Reef, S. E., Abstr., ASM Conf., p. 12 (1993).
Sabesan, S. and R. U. Lemieux, 1984, *Experimentia.* 31:662–1181.
Sabesan et al., *Can. J. Chem.* 62:644–654 (1984).
Sato, K. et al., *Mol. Immunol.* 31:371–381 (1994).
Shepherd, M. G., Ann Rev. Microbiol, 39:579 (1985).
Smith, P. K., et al., Anal Biochem., 150:76 (1985).
Staddon, W. T., et al., Can J. Microbiol, 36:336 (1989).
Wong, S. S., *Chemistry of Protein Conjugation and Cross-Linking*, CRC Press, Boca Raton, Fla. (1991).

3. BACKGROUND OF THE INVENTION

*Candida albicans*, a dimorphic, imperfect yeast, is a significant human pathogen that can cause superficial or invasive diseases (Staddon), and is the most common cause of candidiasis. *C. albicans* can be isolated from the oral cavity of approximately 40% of healthy, asymptomatic individuals. *C. albicans* is considered to be an opportunistic pathogen that primarily infects immunocompromised or immunosuppressed individuals (Cox, Reef, Shepherd).

Cutaneous candidiasis is usually treated with antifungal agents, such as nystatin, ciclopirox, and imidazole creams. For oral and vaginal candidiasis, the drug may be administered in the form of a topical cream, suspension or suppository. In all forms of skin and mucosal candidiasis, relapse after successful treatment is common.

For disseminated candidiasis, such as esophageal or bladder candidiasis, intravenous administration of an antifungal agent, such as amphotericin B is required. Drug side effects with this type of treatment are often severe, and the drugs have limited use because they cannot be administered over an extended time period. Since disseminated candidiasis is a common type of infection in the terminal stages of AIDS infection, the inability to treat the candidiasis successfully has become a widespread disease-management problem.

These problems point to a need for a more effective treatment for candidiasis, both for a disseminated infection which must be treated by intravenous treatment, or localized infection which can be treated topically. Ideally, the treatment method should be effective in reducing or eliminating fungal infection, and have few in any side effects.

4. SUMMARY OF THE INVENTION

The present invention is directed to a method of treating infection by *C. albicans*.

The invention includes, in one aspect, a method of treating an oral or vaginal *C. albicans* infection, and includes administering by topical application to the infected site, a pharmaceutically effective amount of a composition containing βGalNac(1-4)βGal, preferably in the form of conjugates composed of a carrier structure and multiple βGalNac(1-4)βGal moieties attached to the structure.

The conjugates may be βGalNac(1-4)βGal-polypeptide conjugates in which the polypeptide is the carrier structure, and the βGalNac(1-4)βGal moieties are attached to amino groups on the protein through amide linkages. One preferred βGalNac(1-4)βGal moiety has the form βGalNac(1-4)βGal-O(CH$_2$)$_n$CO—, where n=1–10.

Alternatively, the conjugates may be βGalNac(1-4)βGal-polysaccharide conjugates in which the polysaccharide is the carrier structure, and the βGalNac(1-4)βGal moieties are attached to amino groups on polysaccharide through amide linkages.

Alternatively, the conjugates are βGalNac(1-4)βGal-solid-particle conjugates in which the solid particle is the carrier structure. The solid particles may be, for example, silica particles, where the βGalNac(1-4)βGal moieties are linked to the particles through covalent linkages.

In another aspect, the invention includes a method of treating systemic or disseminated infection by *Candida albicans* in an individual in need of such treatment. The method includes administering by parenteral route, a pharmaceutical effective amount of a humanized form of a mouse monoclonal antibody produced by mouse hybridoma cell line Fm16 or cell line PK99H.

Also contemplated by the invention is a purified peptide fragment of *Candida albicans* fimbrial protein which (i) contains less than about 20 amino acid residues that are homologous to a fimbrial protein sequence, and (ii) binds to the monoclonal antibody produced by mouse hybridoma cell line Fm16 or cell line PK99H, or to βGalNac(1-4)βGal moieties.

These and other objects and features of the invention will becomes more fully apparent when the following detailed description of the invention is read in conjunction with the accompanying drawings.

DETAILED DESCRIPTION OF THE INVENTION

I. Definitions

The term "antibody" as used herein, and particularly as used in the context of a therapeutic, means a protein molecule derived from any of the major vertebrate immunoglobulin classes, such as IgA, IgD, IgE, IgG, or IgM. The term "antibody" is understood to encompass fragments of native antibodies, such as $FAB_2$ fragments and $F_C$ fragments.

Antibodies of the invention may be isolated from a hybridoma cell, the serum of a vertebrate, recombinant eukaryotic or prokaryotic cells transformed with antibody coding sequences, including plant cells, ascites fluid, bovine milk, or the like.

The term "human antibody" refers to an antibody which is substantially human in structure; that is, it derives at least its constant regions from a human antibody.

The term "humanized antibody" refer to a type of human antibody which is a hybrid an antibody from a non-human vertebrate species, such as a mouse, a monkey or a rabbit, and a human antibody. Humanized antibodies include chimeric antibodies, whose heavy and light chain constant regions are coded for by a human immunoglobulin coding sequence and whose variable regions are coded for by a non-human species, and CDR-grafted antibodies, which have variable region framework regions as well as heavy and light chain constant regions that are coded for by a human immunoglobulin coding sequence.

As used herein the terms "light chain" or "L" and "heavy chain" or "H" refer respectively to the low and high molecular weight polypeptide subunits which combine to form the basic unit of the antibody molecule as the disulfide-linked tetramer $H_2L_2$.

Figure 17A:
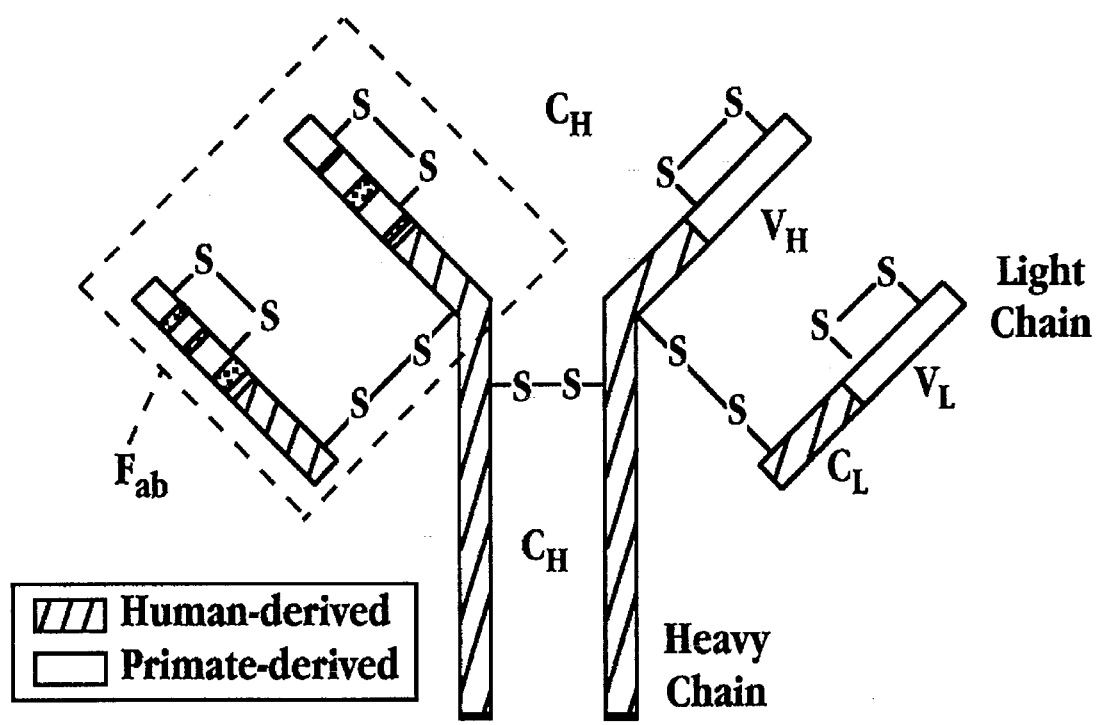
FIG. 17 shows a schematic of a CDR grafted antibody formed in accordance with the invention.

Each light and heavy chain contains a constant (C) region at its carboxyl-terminus and a variable (V) region at its amino-terminus, as depicted in FIG. 17A. The light chain variable region is also referred to as $V_L$, and the heavy chain variable region is referred to as $V_H$.

The term "antigen" refers to a molecule which is specifically recognized and bound by an antibody. An antigen which elicits an immune response in an organism, as evidenced by production of specific antibodies within the organism is termed an "immunogen." The specific portion of the antigen or immunogen which is bound by the antibody is termed the "binding epitope" or "epitope."

The "antigen binding site" is that region of the antibody molecule contained within in the variable regions of the antibody which directly participates in binding the antigen. Generally, the antigen binding site is comprised of specific portions of the variable regions of the anti-body, termed "hypervariable regions" or "complementarity determining regions" (CDR), depicted in FIGS. 17A and 17B. Those portions of the variable regions surrounding or flanking the hypervariable regions are termed "framework regions" (FR).

The term "fimbrial subunit" as used herein, refers to the predominant 66 kDa glycoprotein that is the predominant component of fimbriae isolated from Candida albicans.

The term "adhesin" refers generally to molecules present on a microbial cell or appendage, such as a fimbria, that mediate adherence of the microbe to a cell that is susceptible to infection by the microbe.

The term "Candida fimbrial adhesin protein" refers to the 66 kDa fimbrial subunit glycoprotein characterized herein.

II. Purified Candida albicans fimbrial Protein

Candida albicans possess fimbriae, which are long filiamentous structures that protrude from the cell surface (Gardiner). This section describes the isolation and characterization of the fimbrial structures. As will be seen in the section below, the fimbriae are useful in generating antibodies effective in blocking C. albicans binding to epithelial cells, and in identifying compounds capable of blocking this binding.

A. Isolation of Candida fimbriae

Fimbriae are purified from the yeast phase of C. albicans according to the methods described in Example 1. Briefly, C. albicans cells are cultured and harvested according to standard methods, then subjected to homogenization to shear off fimbriae. The fimbriae are then separated from the cellular material by centrifugation. The resulting supernatant is then processed to yield a crude fimbriae (CF) preparation.

Figure 1A:
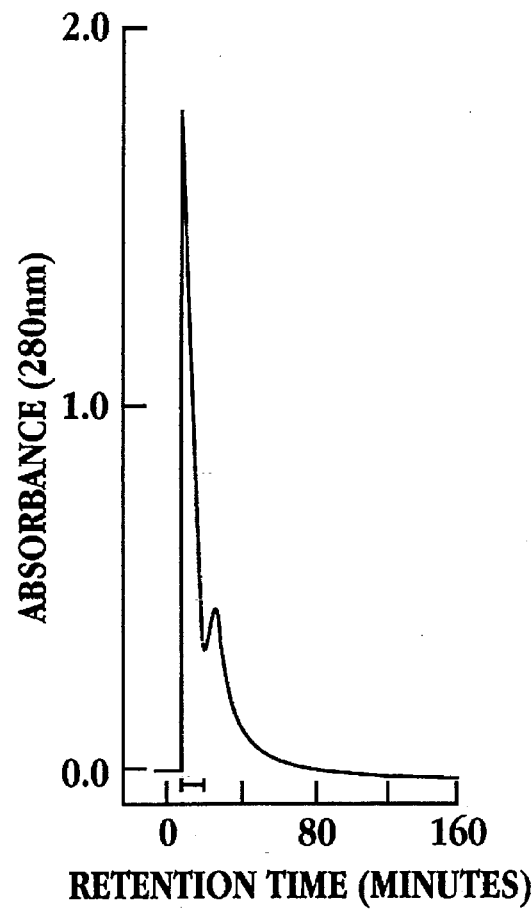
FIG. 1A and FIG. 1B show HPLC chromatograms of separations of CF fimbriae isolated from *C. albicans* (A) and rechromatography of the material eluting in the void volume (major peak) of the elution profile of 1A (1B)

The CF preparation is fractionated by size-exclusion high performance liquid chromatography. The material that elutes in the void volume contains the fimbrial fraction (FIG. 1A). This material is rechromatographed (FIG. 1B) and further processed and concentrated as detailed in Example 1 to yield a fraction termed enriched fimbriae (EF). The presence of the second peak on the rechromatography profile indicates that some of the fimbrial preparations are depolymerized and/or deglycosylated during the purification process. Protein contents of these fractions are determined according to standard methods.

Fimbrial fractions prepared as generally described above, and as detailed in Example 1 can be used to prepare a purified fimbrial protein as described in Example 2 and in the sections below. The EF fraction in particular is useful as an immunogen or antigen for generating antibodies capable of interfering with attachment of Candida to cells via a fimbrial adhesin molecule, such as the fimbrial protein described below. Such antibodies may be generated to combat infection directly, as when the fimbriae is used as a vaccine, or may be isolated and used in passive immunization protocols. The purified fimbrial adhesin protein can likewise be used to produce antibodies useful in the prevention of Candida infections.

B. Purification of Candida fimbrial adhesin protein

Figure 2:
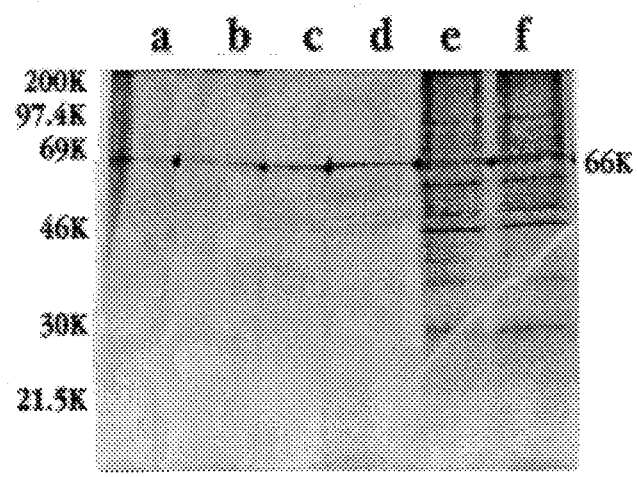
FIG. 2 shows SDS PAGE separation with silver staining of *C. albicans* fimbriae, where lanes a and b contain 5 μg EF fraction, lanes c and d contain 5 μg of semi-enriched fimbriae corresponding to the major peak of FIG. 1A, and lanes e and f contain 10 μg of CF fraction.

Analysis of the fimbrial fractions described above indicated that the major component purified fimbrial structure is a 66 kDa protein, as visualized by SDS PAGE. FIG. 2 shows a silver-stained gel containing fractions from CF (lanes a and b), semi-enriched fimbriae eluted from first HPLC fractionation (lanes c and d) and EF (lanes e and f). As can be seen, the EF preparation consists almost exclusively the 66 kDa protein.

Figure 3:
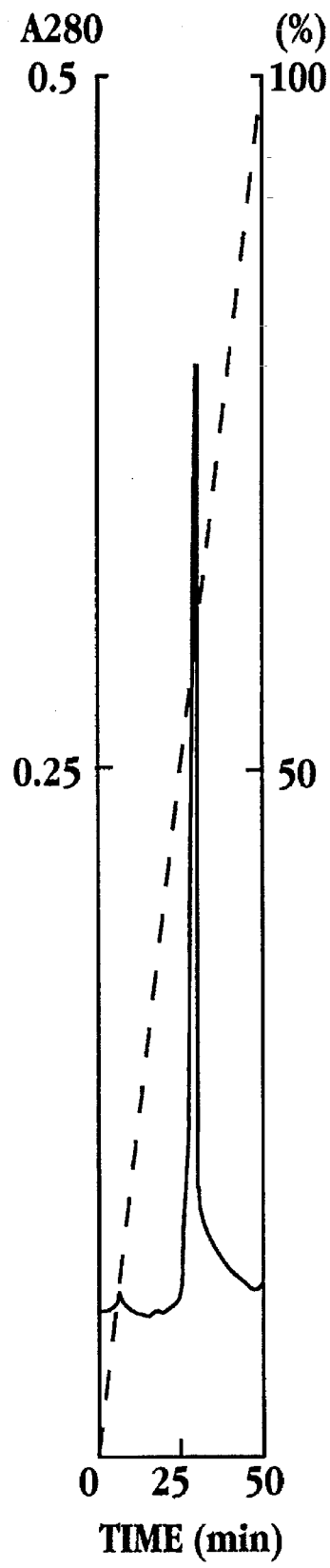
FIG. 3, shows a reversed phase HPLC chromatogram of 66 kDa fimbrial protein electroeluted from SDS PAGE gel.

To further purify the isolated fimbrial protein, gel slices containing the 66 kDa protein are isolated and electroeluted, according to the protocols given in Example 2A, or by other equivalent procedures well known in the art. The eluted protein fraction is further purified by reversed-phase HPLC, according to methods described in Example 2. FIG. 3 shows a chromatograph of a single peak eluting from this column. This peak fraction may be used as a source of purified fimbrial adhesin protein for further characterization.

C. Properties of purified fimbrial protein

The EF preparation was used to determine the protein and carbohydrate composition of the 66 kDa C. albicans fimbrial subunit protein. To this end, a combination of techniques including phenol-sulfuric carbohydrate assay, BCA protein assay and amino acid analysis were used to analyze protein derived from the EF fraction, as detailed in Example 2, parts B and C, and described below. The fimbrial subunit is approximately 85% carbohydrate and approximately 15% protein.

1. Molecular Weight

The molecular weight of the fimbrial subunit protein was determined to be 66,000, as determined by SDS polyacrylamide gel electrophoresis, described in Example 3 and illustrated by the data presented in FIG. 2. The molecular weight of the peptide component of the protein was determined to be 8,644, based on compositional analysis of the peptide, which was found to consist of 79 amino acids, as described below.

2. Protein/carbohydrate composition

The amount of carbohydrate present in the fimbrial protein sample can be determined according to standard methods, one of which is the phenol-sulfuric acid carbohydrate assay detailed in Example 2C. From this assay, in conjunction with the measured protein content of the same sample, the relative percentages of carbohydrate and protein in the sample are determined. In the samples prepared from C. albicans 40 described herein, it was found that carbohydrate comprises about 80–85% of the fimbrial protein, while the peptide portion of the protein constitutes only about 15% of protein.

Further characterization of the carbohydrate portion of the protein can be carried out according to standard procedures, such as the gas chromatographic procedure detailed in Example 2C. Using this method, it was found that the main carbohydrate moiety present in the fimbrial preparation is D-mannose. Several additional minor components were also observed in the samples derived from EF.

3. Amino acid Composition

The amino acid composition of the fimbrial protein subunit is also determined according to standard methods. As described in Example 2B, acid hydrolysis followed by amino acid analysis by automated analyzer was used in experiments carried out in support of the present invention to yield the amino acid composition shown in Table 1. In the table, amino acid values are given as the number of residues determined to be present per protein molecule, with the integer value calculated in parentheses. This analysis, in which no correction was made for cysteine and tryptophan or for the destructive loss of serine and threonine during hydrolysis, indicated that the most frequent amino acid residues of the protein portion of fimbriae were valine (Val), aspartic/asparagine (Asx), glutamic acid/glutamine (Glx), serine (Ser), threonine (Thr), glycine (Gly), leucine (Leu), isoleucine (Ile), lysine (Lys) and alanine (Ala), while little methionine (Met) or histidine (His) was detected. (Standard 3-letter amino acid codes are used in the table.)

TABLE 1

AMINO ACID COMPOSITIONS OF FIMBRIAL SUBUNITS FROM C. ALBICANS STRAIN #40

| Amino Acid Residues | Residues/Fimbrial Subunit |
| --- | --- |
| Asx | $8.24^1(8)^2$ |
| Thr* | 4.73(5) |
| Ser* | 5.73(6) |
| Glx | 8.17(8) |
| Pro | 2.79(3) |
| Gly | 7.02(7) |
| Ala | 6.00(6) |
| Cys | ND |
| Val | 5.57(6) |
| Met | 0.82(1) |
| Ile | 4.73 |
| Leu | 6.82(7) |
| Tyr | 2.55(3) |
| Phe | 3.21(3) |
| His | 1.48(1) |
| Lys | 5.91(6) |
| Trp | ND |
| Arg | 3.81(4) |
| No. of Residues | (79) |
| Estimated MW | 8644 |

[1]Number of residues determined experimentally.
[2]Integer value.
ND Not determined.
*No correction was made for Cys and Trp, or for the destructive loss of Ser and Thr during hydrolysis.

4. Electron microscopic examination of Candida fimbriae

Figure 4A:
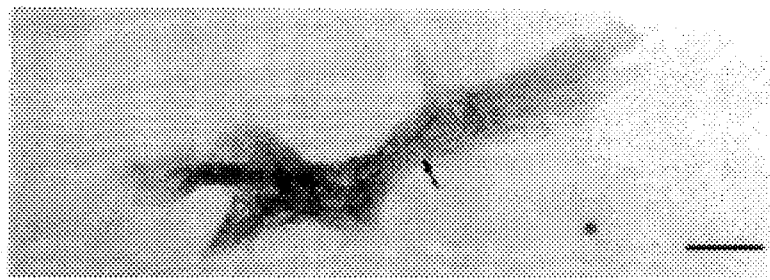
FIG. 4A and FIG. 4B show negatively stained electron micrographs of C. albicans.
Figure 4B:
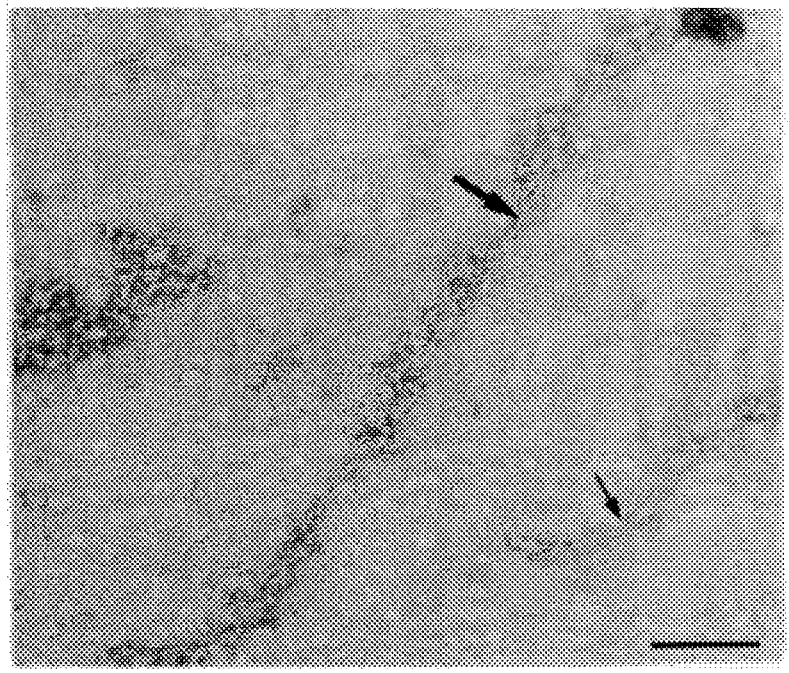
Figure 4C:
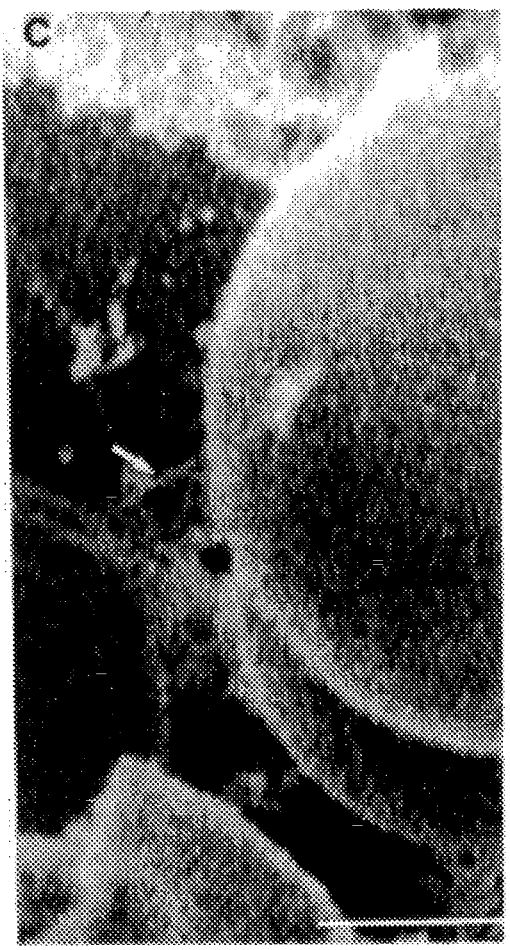
FIG. 4C shows a scanning electron micrograph of C. albicans fimbriae.

FIG. 4 shows negative stain electron micrographs of enriched C. albicans fimbriae (panels A and B). Electron microscopic methods are detailed in Example 3B herein. As can be seen in panel A, fimbriae (highlighted by arrows) are frequently decorated with material and appear to be flexible. The micrographs reveal large numbers of fimbrial structures ~8 nm in diameter. These structures were observed to mediate *C. albicans* binding to BECs. Also apparent from the micrograph in panel B is the observation that fimbriae frequently aggregate to form loosely associated bundles of filaments. Panel C shows a scanning electron micrograph of *C. albicans* fimbriae. In this micrograph a fimbrial attachment structure is stretched between the Candida cell and the epithelial cell, indicated by the arrow. The solid bars represent 1 µm in all micrographs.

In general, the fimbriae appeared as flexible filaments that frequently aggregated into small bundles of fimbriae. The fimbriae protruding from the surface of the yeast as filamentous structures appeared to be sparsely distributed but appeared to mediate binding to BECs, as described above with reference to the structure indicated by the arrow in panel C.

D. Binding properties of Fimbria and Fimbrial proteins

Figure 5A:
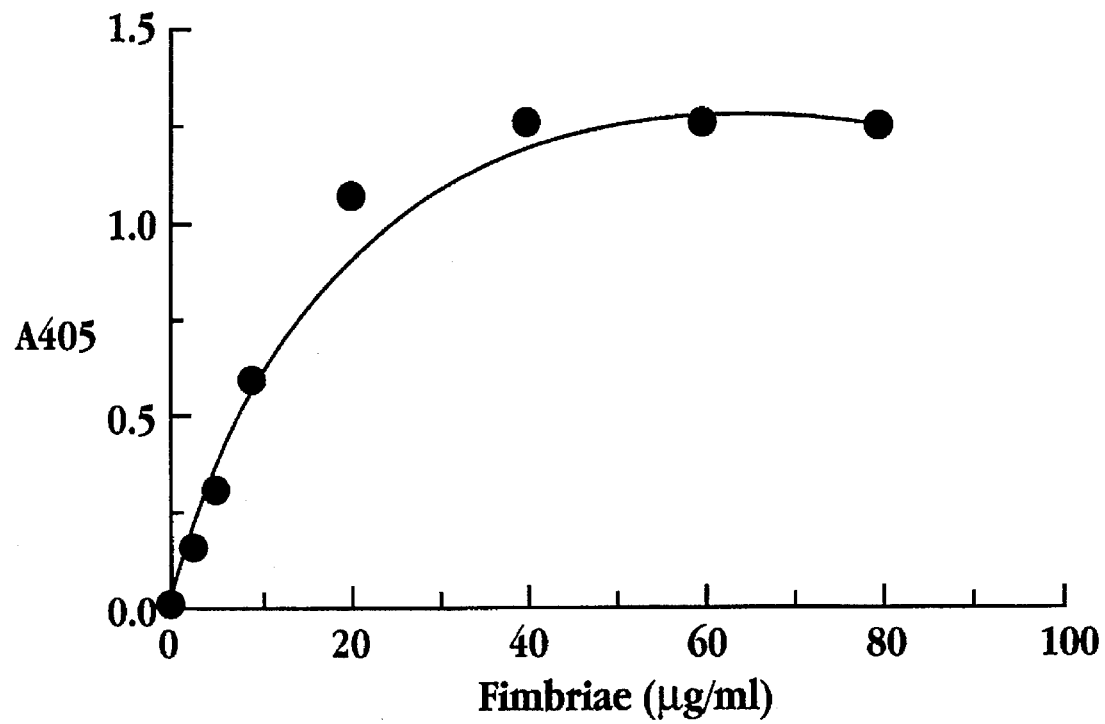
FIG. 5A shows saturation binding of C. albicans fimbriae to human buccal epithelial cells (BECs)

According to an important aspect of the present invention, it has been discovered that Candida fimbriae mediate binding of the fungal cells to target human epithelial cells. FIG. 5A shows the results of a saturation binding assay in which binding of fimbriae to human buccal epithelial cells was determined. In this assay, as detailed in Example 4A, epithelial cells were added to filtration chambers equipped with treated, polycarbonate filters, and aliquots containing varying amounts of EF were added to each chamber. Following washing of the cells to remove unbound fimbriae, mouse anti-*C. albicans* fimbrial antibodies (Fm16) were added to each sample. Fimbrial binding was measured by determining binding of horseradish peroxidase goat anti-mouse antibodies to the preparation, according to standard methods set forth in Example 4. The data plotted indicate that the binding is saturable, with an approximate maximal binding ($B_{max}$) of 50 µg of protein per milliliter. Half maximal binding was observed at 10 µg protein/ml, indicating that binding of the purified fimbrial preparation to the cell surface receptors is of high avidity or affinity.

Figure 5B:
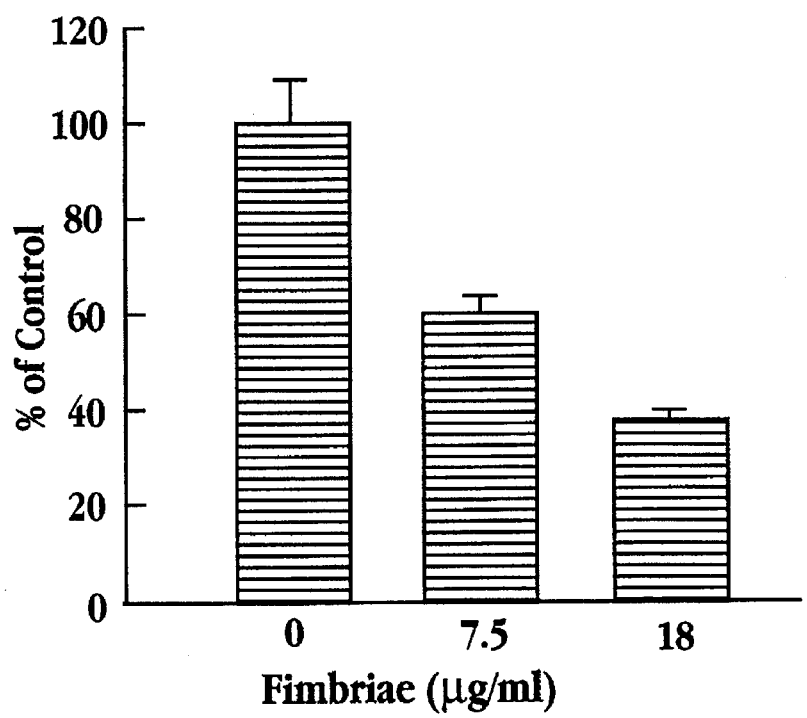
FIG. 5B shows a plot of inhibition of C. albicans whole cell binding to human BECs by direct competition with EF.

The ability of the purified (EF) fimbrial preparation to interfere with binding of native Candida fungal cells to buccal epithelial cells (BECs) was measured in further experiments, as described in Example 4B. In these assays, BECs were pre-incubated with fimbrial EF fraction, then incubated with *Candida albicans* yeast cells. FIG. 5B shows the results of experiments in which two concentrations of EF fimbriae were tested for ability to interfere with Candida binding. As illustrated, at a concentration of 7.5µg/ml, EF fimbria were able to inhibit by about 40%, binding of Candida to whole BECs. This result correlates well with the half maximal binding concentration of the fimbria for the BECs, providing additional support for the high affinity of this binding interaction.

III. βGalNac(1-4)βGal Conjugates

A. Preparation of βGalNac(1-4)βGal Conjugates

Figure 6:
FIG. 6 shows a shorthand representation of the βGalNa-c(1-4)βGal conjugate of the invention.

The conjugates for use in the treatment method of the invention (FIG. 6) are composed of multiple βGalNac(1-4)βGal (GNG) moieties attached to suitable multivalent carriers. In general, the conjugates are constructed so as to render the portions of the GNG moiety which are distal from the reducing end accessible for binding to *C. Albicans* fimbriae. Preferably, each GNG moiety is linked to the carrier through the C-1 carbon of the terminal GNG Gal unit. The distance between the GNG moiety and the carrier surface or backbone is controlled by suitable choice of the group (S) linking the GNG moiety to the carrier, as illustrated below. Preferably, the distance between the C-1 carbon of GNG and the backbone or surface of the carrier is between about 5 and 25 Å, as measured based on full extension of the linking group.

Figure 7A:
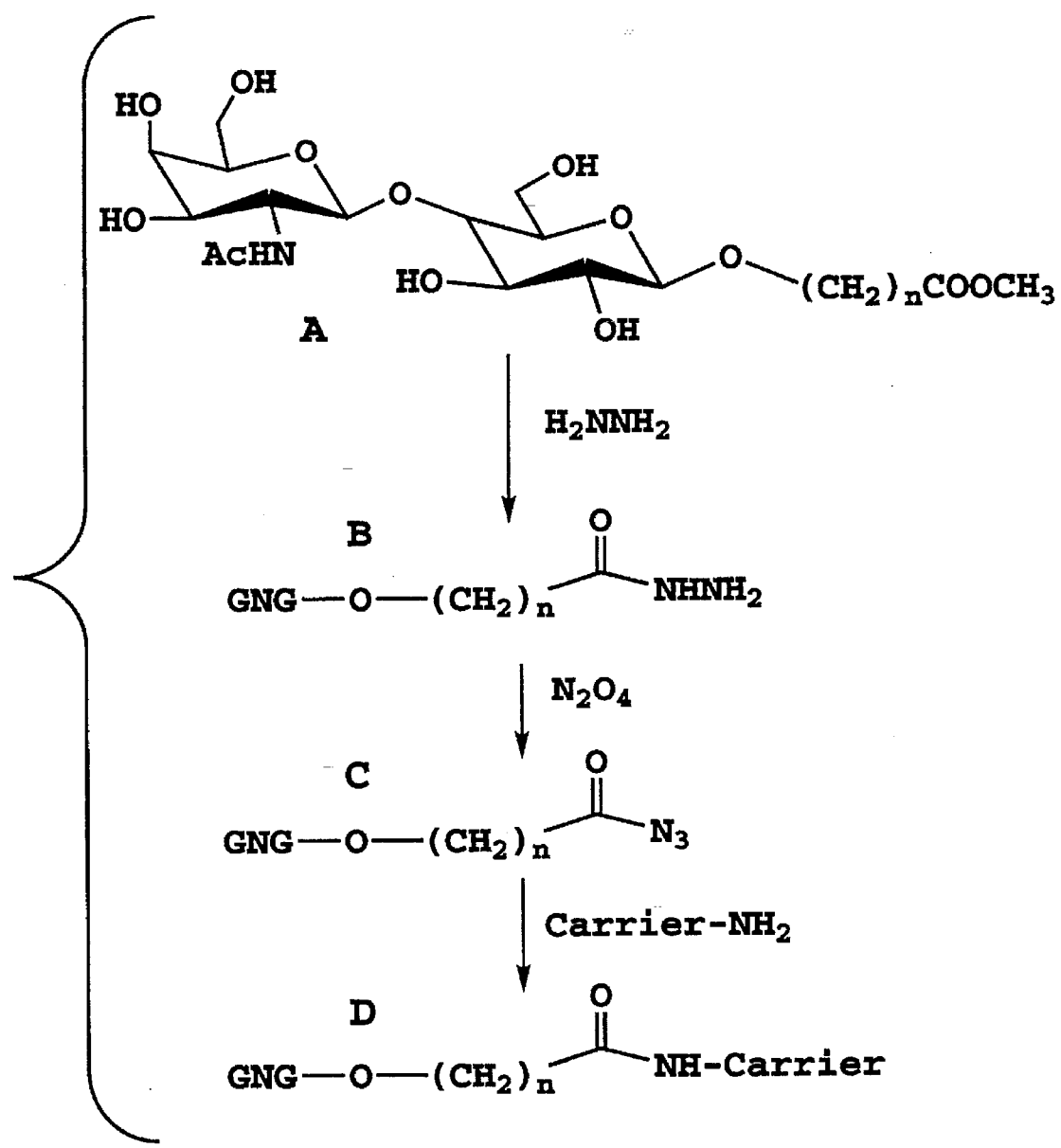
FIGS. 7A–7C show reaction schemes for preparing conjugates in accordance with the invention from a βGalNa-c (1-4)βGal ester compound.

One GNG compound, βGalNac(1-4)βGal-O(CH$_2$)$_n$CO$_2$CH$_3$ (A), which is a useful precursor for preparing conjugates in accordance with the invention is shown at A at FIG. 7A. Methods for preparing such compounds have been described (e.g., Sabesan et al., 1984; Lemieux, 1979), or can be obtained from commercial sources (e.g., Chem-biomed Inc.).

As shown, compound A consists of a βGalNac(1-4)βGal moiety joined by an ether linkage at C-1 of the Gal group to an alkylcarboxy ester group ((CH$_2$)$_n$CO$_2$CH$_3$). The length of the alkyl carboxy group depends on the ester alcohol precursor (HO(CH$_2$)$_n$CO$_2$CH$_3$) used in the synthesis. Typically, n is 1–10, and preferably, 2–8.

Compound A may be made more amenable to coupling to a carrier by conversion to a hydrazide by the method of Pinto et al. (1983). In brief, the methyl ester is reacted with hydrazine in ethanol to form hydrazide product B (FIG. 7A). Compound A (0.09 mmol, 1 equiv) is dissolved in a mixture of absolute ethanol (0.3 ml) and hydrazine hydrate (0.1 mL). After 18 h at 20° C., the solution is evaporated to a syrup, which is then co-evaporated twice with water (2 mL). The product is dissolved in distilled water (2 mL) which is then lyophilized to dryness.

With continued reference to FIG. 7A, treatment of the resultant hydrazide B with dinitrogen tetraoxide affords azide compound C. The transformation is effected by preparing a solution of hydrazide B (29 µmol) in freshly distilled dimethylformamide (0.4 mL) stirred at −40° to −50° C., and adding a standardized stock solution of dinitrogen tetraoxide in dichloromethane (37 µmol, 0.46M) using a syringe pre-cooled with dry ice. The temperature of the reaction is maintained for 15 minutes at −20° to −10° C., after which the mixture is ready for immediate reaction with amine-containing carrier to produce conjugate D.

Figure 7B:
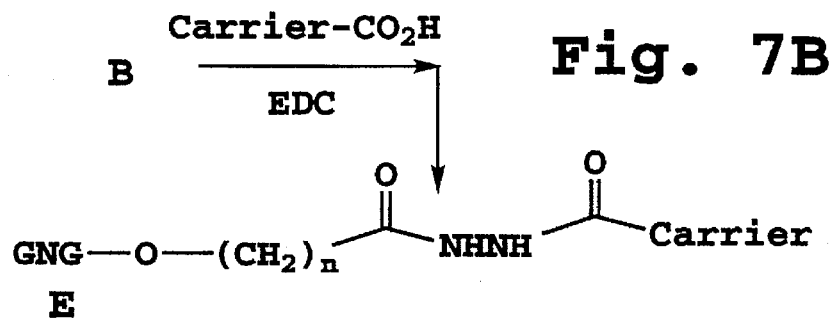

Alternatively, a GNG hydrazide compound such as hydrazide B is coupled to a multi-carboxylated carrier using a suitable coupling agent, e.g., 1-ethyl-3-(3-dimethylaminopropyl)-carbodiimide (EDC) or the like, to form an amide linkage between the GNG moiety and the carrier (conjugate E, FIG. 7B). Again, the spacing between the GNG moiety and the carrier is determined by the number (n) of methylene groups in the GNG-hydrazide starting material.

Figure 7C:
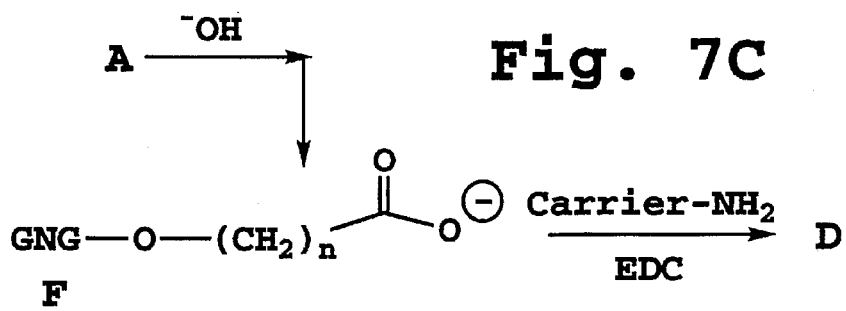

This approach can be applied in reverse (FIG. 7C), by hydrolyzing compound A in the presence of base (e.g., aqueous sodium hydroxide) to convert the carboxylate ester in A to a free carboxylate F (or its sodium salt). Carboxylate derivative F can then be coupled to an amine-containing carrier to produce a conjugate (D) linked by an amide bond.

In another general approach, GNG-carrier conjugate is prepared from a GNG moiety consisting of βGalNac(1-4)βGal coupled at its reducing end to one or more additional saccharide units having a reducing sugar with a C-1 hemiacetal group as the terminal saccharide unit. Oxidation of the hemiacetal group, by reaction with sodium periodate, for example, converts the hemiacetal group to a non-cyclic C-1 carboxylic acid. Although the cyclic structure of the terminal sugar group is disrupted by these reaction conditions, the βGalNac(1-4)βGal moiety remains chemically unaltered. The free carboxylate can then be coupled to an amine-containing carrier using EDC, for example, to create an amide linkage.

Figure 8:
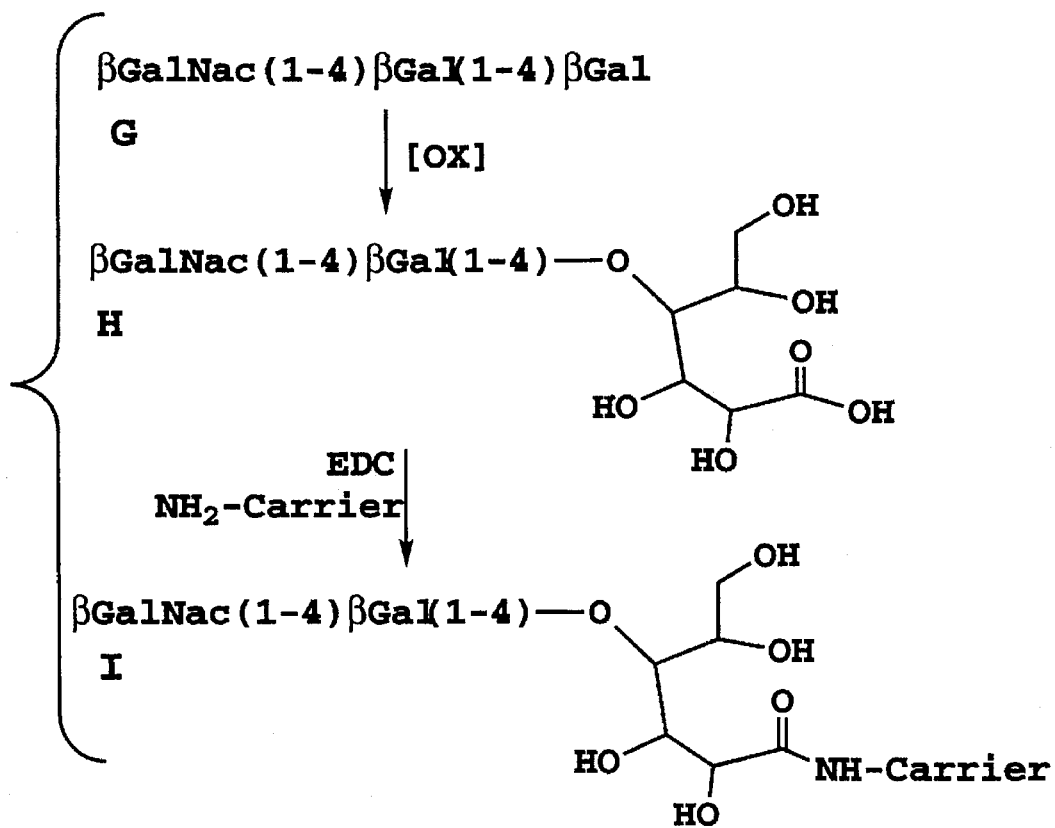
FIG. 8 shows a reaction scheme for preparing a βGalNa-c(1-4) βGal conjugate using a polysaccharide starting material.

The approach is illustrated in FIG. 8. Reaction of GNG-trisaccharide G (prepared by the general methods in Sabesan et al. 1984, for example) with sodium periodate affords the ring-opened carboxylate compound shown at H. Reaction of the carboxylate compound with an amine-containing carrier in the presence of EDC affords conjugate I. As can be seen, the GNG moiety remains intact throughout the reaction sequence and is accessible in conjugate I for binding to *C. albicans* fimbriae.

Furthermore, the ring-opened terminal saccharide provides a linking group which separates the GNG moiety from the carrier. If a longer linking group is desired, a longer GNG-polysaccharide, such as a tetrasaccharide, can be used in place of GNG-trisaccharide to produce a conjugate in which the GNG moiety is spaced from the carrier by two or more saccharide units. Where a GNG-tetrasaccharide is used, for example, the linkage between the GNG and carrier moieties consists of a cyclic saccharide unit linked to a terminal, ring-opened saccharide unit.

It will be appreciated that GNG-polysaccharides for use in this approach may also be prepared enzymatically using suitable glycosyltransferases.

Figure 9:
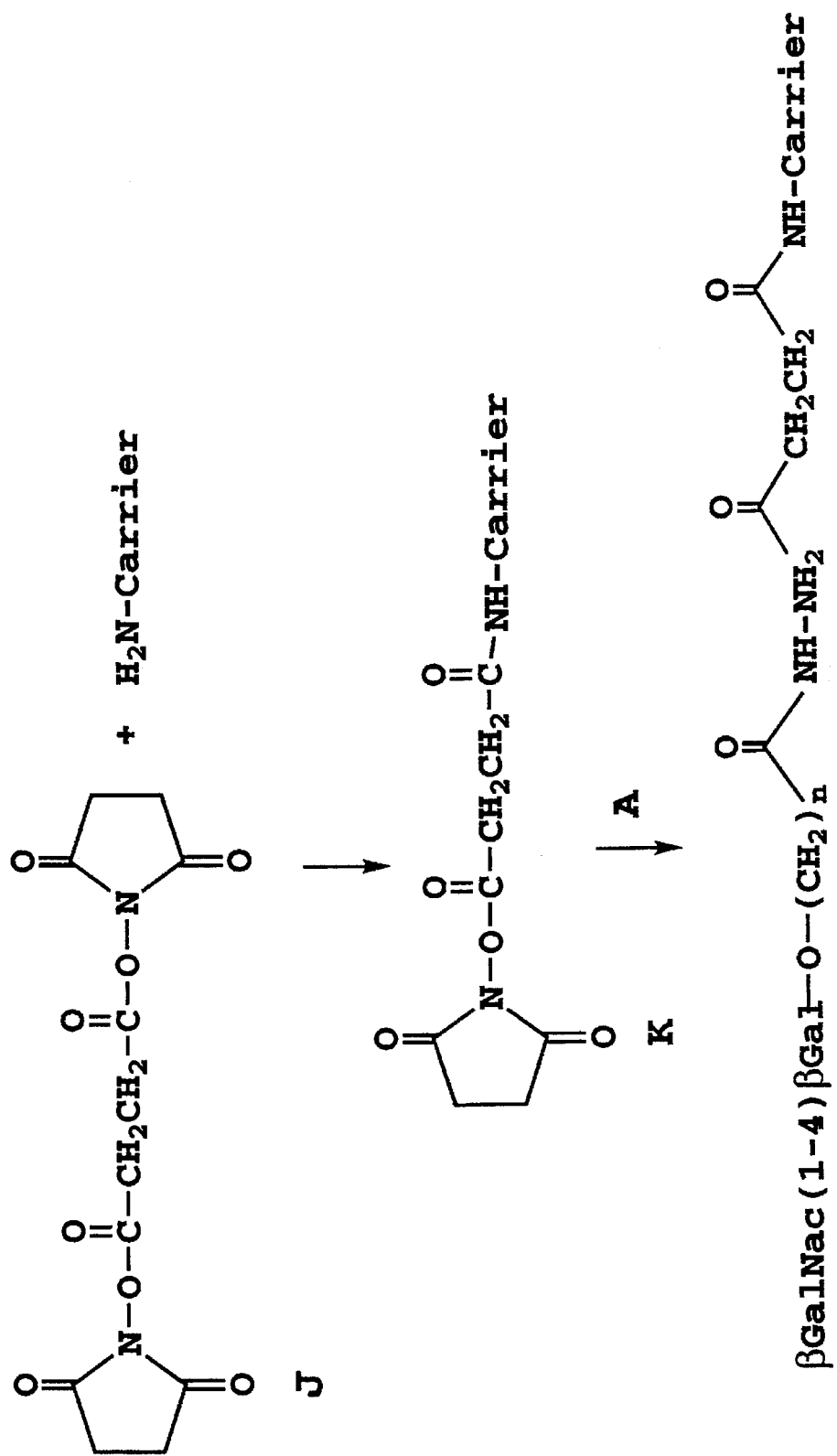
FIG. 9 shows a reaction scheme for preparing a βGalNa-c(1-4) βGal conjugate using a bifunctional crosslinking agent.

In yet another approach (FIG. 9), a GNG-hydrazide derivative such as A in FIG. 7A is coupled to an amine-containing carrier using a homobifunctional crosslinking reagent such as succinate bis-(N-hydroxysuccinimide ester J, or the more water-soluble homolog, bis-(sulfosuccinimidyl)suberate (Wong, 1991, e.g., page 57 and Chapter 4 therein). Preferably, the amine-containing carrier is first reacted with excess crosslinking agent to convert most or all of the carrier amino groups to derivatives terminating in activated ester groups, as illustrated at K in FIG. 9. After removal of excess reagent, e.g., by gel filtration chromatography, the derivatized carrier is reacted with the GNG-hydrazide A to afford GNG-carrier conjugate L.

It will be appreciated that other coupling methods known in the art (e.g., Wong, 1991) may also be used to produce additional conjugates in accordance with the invention.

The carrier moieties which are used in the GNG conjugate of the invention may take any of several forms. In one embodiment, the carrier is a polypeptide, that is, a protein or peptide, having multiple sites for attachment of the BGalNac (1-4)β moiety. Exemplary proteins for preparing conjugates include bovine serum albumin, keyhole limpet hemocyanin, ovalbumin, and thyroglobulin, for example. The protein can be reacted with a GNG-azide compound, as in the last step of the scheme shown in FIG. 7A, to afford an amide linkage between protein amino groups and the GNG compound. The protein can also be coupled by EDC to a GNG-carboxylate derivative, e.g., the base-hydrolysis product F obtainable from A.

Alternatively, the carrier can be a synthetic peptide prepared by standard peptide synthesis methods and preferably containing 4 to 50 amino acid residues and 4 to 25 lysyl or glutamate residues. Preferably, the peptide is a polyamino peptide, e.g., a polylysine peptide such as $Lys_4$ or $Lys_{25}$, or a multi-lysine containing peptide in which the lysyl residues are separated by one or two non-lysyl residues, for example. Such carriers are then joined to suitable GNG-moieties by amide linkages using the approaches described above.

In a second general embodiment, the carrier used for the GNG-conjugate is a polyaminopolysaccharide consisting of a polysaccharide backbone having multiple amino groups to which the βGalNac(1-4)βGal moieties are attached. Such polyaminopolysaccharides may be linear or macrocyclic (e.g., cyclodextrin) and can be obtained from natural sources or prepared synthetically (e.g., see Ogura et al., 1992, Chapters 12 and 18).

For example, a polyhexose such as amylose or a polymaltose can be derivatized with acetyl groups to block all free hydroxyls. The blocked polysaccharide is then treated with excess ammonia or excess ethylene 1,2-diamine under conditions effective to selectively displace the acetyl group attached to the primary carbons at C-6 in each saccharide unit. De-acylation under basic conditions results in a polysaccharide having amino groups at C-6.

Where the polysaccharide is a linear or branched polysaccharide, the polysaccharide preferably contains 4–25 amino groups capable of attachment to GNG-moieties. Alternatively, where the polysaccharide is an α- or β-cyclodextrin, the polysaccharide usually contains 6 or 7 amino groups.

In another general embodiment, the carrier used for the GNG-conjugate is a solid-particle. The particles are sized so as to provide a non-gritty solution when suspended in aqueous solution. In one preferred embodiment, the solid-particles consist of silica, suitably derivatized for coupling to a GNG moiety. Methods for derivatizing silica with a number of functional groups are well known (e.g., Wong, 1991), and derivatized materials are also available from commercial sources.

The functional groups are preferably amino groups or carboxyl groups, although others (e.g., thiols) may be used. Amino groups can be added to silica by silylation with an aminoalkyl trialkoxysilane, for example. Carboxyl groups can be added by reacting amino-derivatized silica with succinic anhydride, for example.

The manner in which the GNG moiety is joined to the solid-particle carrier is generally the same as for the polypeptide and polysaccharide carriers noted above.

Other materials which are useful as solid-particles include dextran, agarose, and latex, for which comparable derivatization methods are known.

B. Binding of *C. albicans* fimbriae to GNG

In accordance with one aspect of the invention, it has been discovered that *Candida* fimbriae bind to certain glycosphingolipids, notably asialo-$GM_1$ [gangliotetraosylceramide: βGal(1-3)βGalNAc(1-4)βGal(1-4)βGlc(1-1)Cer].

Figure 10:
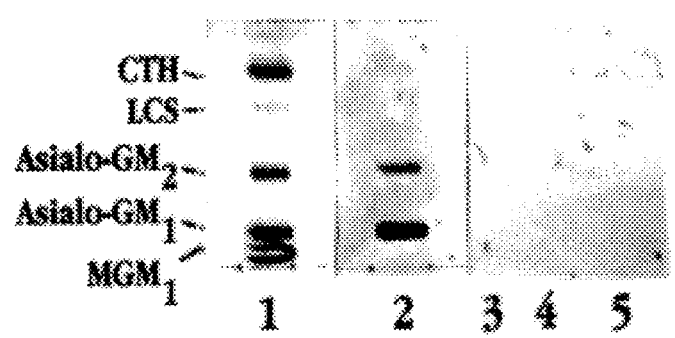
FIG. 10 shows binding of C. albicans fimbriae to glycosphingolipids separated by thin layer chromatography (TLC)

FIG. 10 shows the results of studies in which *Candida* fimbriae were tested for ability to bind to a number of glycolipids separated on thin layer chromatography (TLC) plates, according to methods detailed in Example 5. Bound fimbriae on the TLC plates were visualized with a Protein G affinity-purified anti-*C. albicans* fimbriae monoclonal antibody, Fm16, obtained from ascites tumor in Balb/c mice as described below and a goat anti-mouse IgG alkaline phosphatase. Normal mouse IgG, which does not bind to *C. albicans* fimbriae was used as a control in these studies. The results shown in FIG. 10 show that *C. albicans* fimbriae bind specifically to asialo-$GM_1$ [gangliotetraosylceramide: βGal (1-3)βGalNAc(1-4)βGal(1-4)βGlc(1-1)Cer] and asialo-$GM_2$ [gangliotriosylceramide: βGalNAc(1-4)βGal(1-4) βGlc(1-1)Cer] (Lane 2). A normal mouse IgG control which was used instead of Fm16 failed to detect fimbrial binding to asialo-$GM_1$ and asialo-$GM_2$ (FIG. 10, lanes 3 and 4) as the normal mouse IgG does not bind to fimbriae. Fimbriae failed to bind to $GM_1$, lactosyl cerebroside (LCS) or ceramide trihexoside (CTH) [aGal(1-4)βGal(1-4)βGlc(1-1)Cer]. The lack of binding to $GM_1$ indicates that removal of the sialic acid moiety of $GM_1$ may be necessary for fimbrial protein binding. Lane 1 shows the migration positions of glycosphingolipids CTH, LCS, asialo-$GM_2$, asialo-$GM_1$ and $MGM_1$ as indicated by charring of the plate.

Figure 11A:
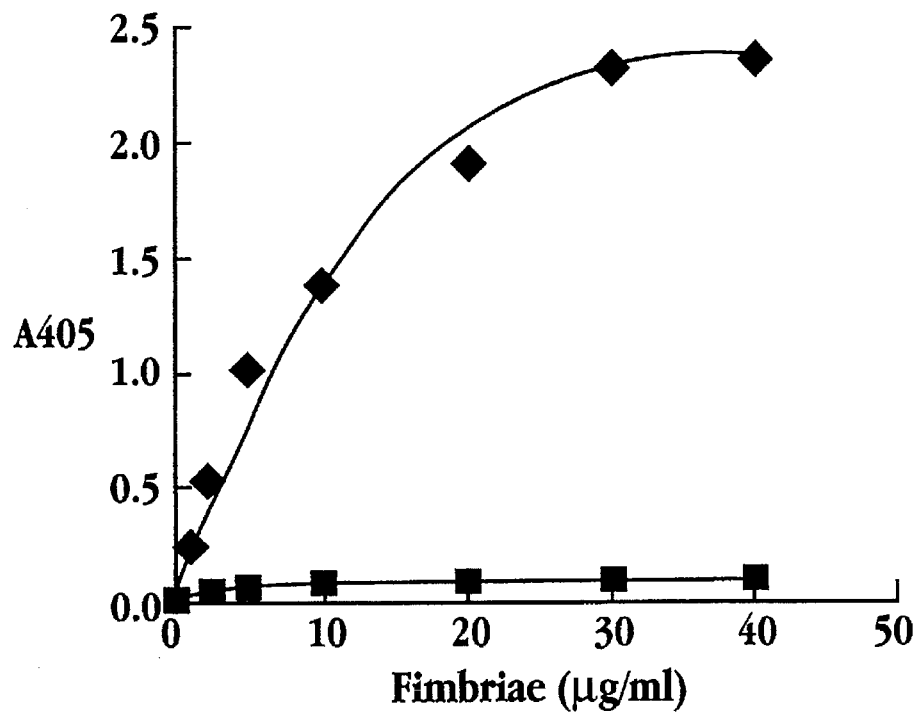
FIG. 11A shows binding of C. albicans fimbriae to asialo-$GM_1$ (diamonds) and CTH (squares)

Binding of *Candida* fimbriae to GSLs was further assessed using an assay in which GSLs were immobilized on microtiter plates. In these assays, detailed in Example 8, *C. albicans* fimbriae were found to bind to asialo-$GM_1$ in a saturable, concentration-dependent manner. FIG. 11A shows results of experiments in which increasing concentrations of EF fimbriae (ranging from 0 to 4 µg/0.1 ml well) were tested for ability to bind asialo-GM$_1$ (diamonds) and CTH (squares) immobilized in microtiter wells (0.5 µg/well). The amount of fimbriae bound is represented as the absorbance values measured at 405 nm. The concentration of fimbrial protein required for half-maximal binding was determined to be 8 µg/ml under the assay conditions, indicating a reasonably high affinity of fimbriae for asialo-GM$_1$. Fimbriae failed to bind to CTH (squares) coated on wells.

Figure 11B:
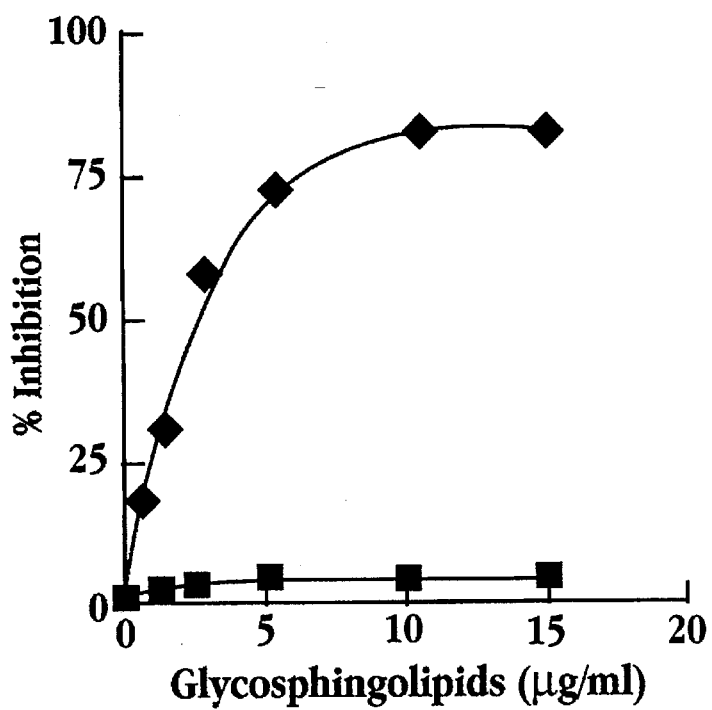
FIG. 11b shows inhibition of C. albicans fimbrial binding to asialo-$GM_1$ (diamonds) and CTH (squares)

The binding specificity to GSLs was assessed in experiments in which free GSLs were tested for their abilities to inhibit binding of C. albicans fimbriae to immobilized GSLs. These experiments were carried out using the microtiter plate assay described above, and as further detailed in Example 5B. C. albicans fimbriae (50 µg/ml) were preincubated with varying concentrations of asialo-GM$_1$ or CTH at 37° C. for an hour prior to addition into the precoated microtiter wells. In this assay, GSLs were suspended in phosphate buffered saline (PBS) at a sufficiently low concentration to prevent micellar formation. C. albicans fimbriae binding to immobilized asialo-GM$_1$ was reduced by 78% (Diamonds, FIG. 11B) by asialo-GM$_1$. No competition of fimbriae binding to CTH was observed (squares). The concentration of asialo-GM1 required for half-maximal inhibition is 1.44 µg/ml.

Further experiments to determine the specificity of fimbrial binding to GSLs were carried out using a plate binding assay, as described above, but immobilizing on the plates a βGalNAc(1-4)βGal-BSA conjugate, synthesized from βGalNAc(1-4)βGal-O(CH$_2$)$_8$COOCH$_3$ (Sabesan and Lemieux), as described in Part B, above. The coupling ratio of disaccharide: BSA was 12:1. The protocol utilized for this assay was similar to that employed for the assessment of C. albicans fimbriae binding to GSLs except that the plates were coated with 100 µl/well of a 10 µg/ml solution of synthetic βGalNAc(1-4)βGal-BSA conjugate in 0.01M carbonate buffer, pH 9.5.

Figure 12A:
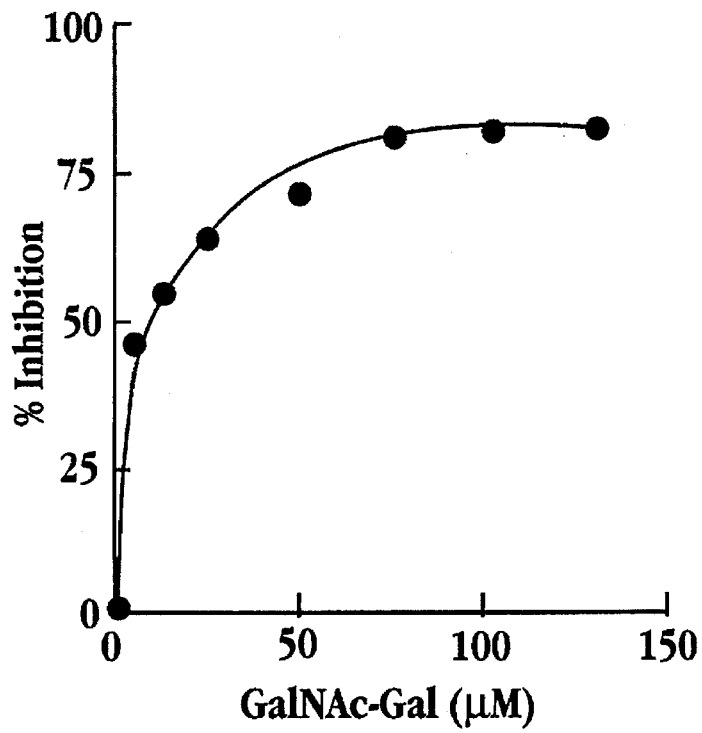
FIGS. 12A and 12B show inhibition of fimbrial binding to βGalNac(1-4)βGal-BSA conjugate by βGalNac(1-4)βGal (12A) and by asialo-$GM_1$ (12B)
Figure 12B:
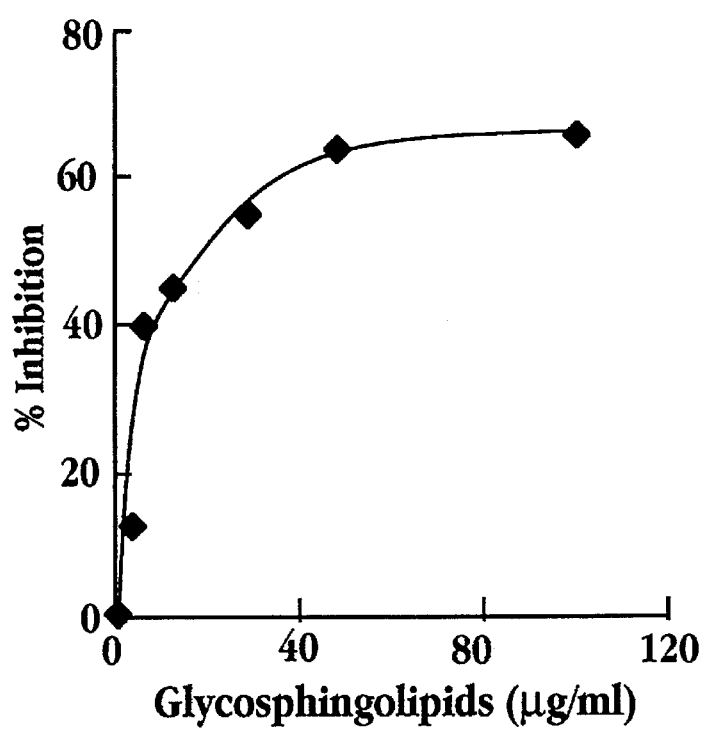

Using this assay, it was first determined that fimbriae bind to the βGalNAc(1-4)βGal-BSA conjugate in a saturable, concentration-dependent manner. FIGS. 12A and 12B show the results of experiments in which compounds were tested for ability to inhibit binding of fimbriae to the βGalNAc(1-4)βGal-BSA conjugate. The protocol used in this assay was similar to the one used in the GSL inhibition assay described above, except that the plates were coated with 100 µl/well of a 10 µg/ml solution of synthetic βGalNAc(1-4)βGal-BSA conjugate in 0.01M carbonate buffer, pH 9.5. As depicted in FIG. 12A, βGalNAc(1-4)βGal-methylester ("GalNAcGal") was able to inhibit binding to the GalNAcGal-BSA conjugate in a concentration dependent manner. Half-maximal inhibition was attained at 8.2 µM of βGalNAc(1-4)βGal-methylester, indicating a highly specific interaction. Furthermore, when asialo-GM$_1$ was employed as the competitor in this assay, the ganglioside also competitively inhibited C. albicans fimbriae binding to βGalNAc(1-4)βGal-BSA conjugate (FIG. 12B). The concentration of asialo-GM$_1$ required for half-maximal inhibition was 7.5 µg/ml.

C. Inhibition of C. albicans binding to BECs by βGalNac(1-4)βGal and βGalNac(1-4)βGal-conjugates Further experiments carried out in support of the present invention demonstrate the ability of synthetic βGalNAc(1-4)βGal-methyl ester or glycosphingolipids to inhibit binding of Candida fimbriae to whole epithelial cells (BECs).

Figure 13A:
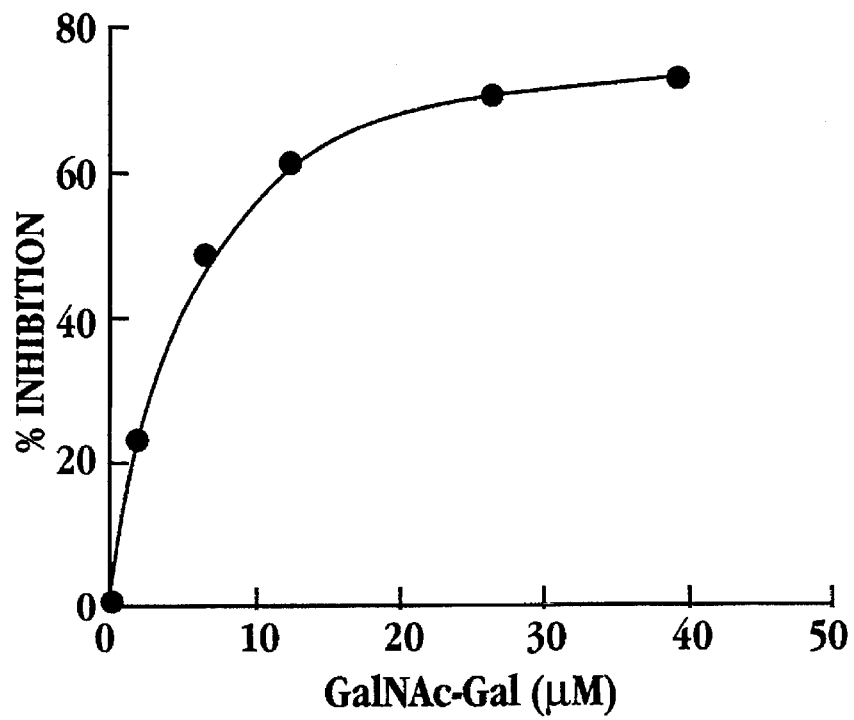
FIGS. 13A–13C show inhibition of fimbrial binding to BECs by βGalNac(1-4)βGal (13A), asialo-$GM_1$ (13B, diamonds) or CTH (13B, squares), and inhibition of C. albicans binding to BECs by βGalNac(1-4)βGal.

FIG. 13 shows the results of experiments in which C. albicans fimbriae were preincubated with either βGalNAC (1-4) βGal-methylester (circles, panel A), asialo-GM1 (diamonds, panel B) or CTH (squares, panel B) for an hour at 37° C. prior to addition of 2.0×10$^5$ BECs. The percent inhibition is the inhibition of binding in the presence of the competing antigens with respect to binding observed in the absence of any competitors.

Figure 13B:
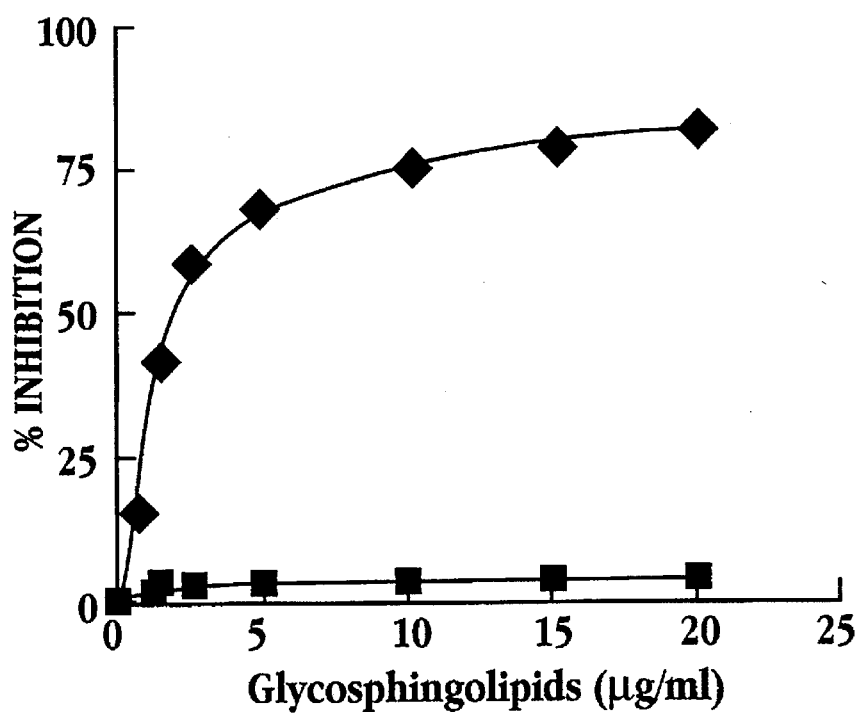

These experiments show that βGalNAc(1-4)βGal-methylester (FIG. 13A) and asialo-GM$_1$ (FIG. 13B) inhibit C. albicans fimbriae binding to BECs by 70% and 80%, respectively. CTH failed to inhibit C. albicans fimbriae binding to BECs (FIG. 13B).

Figure 13C:
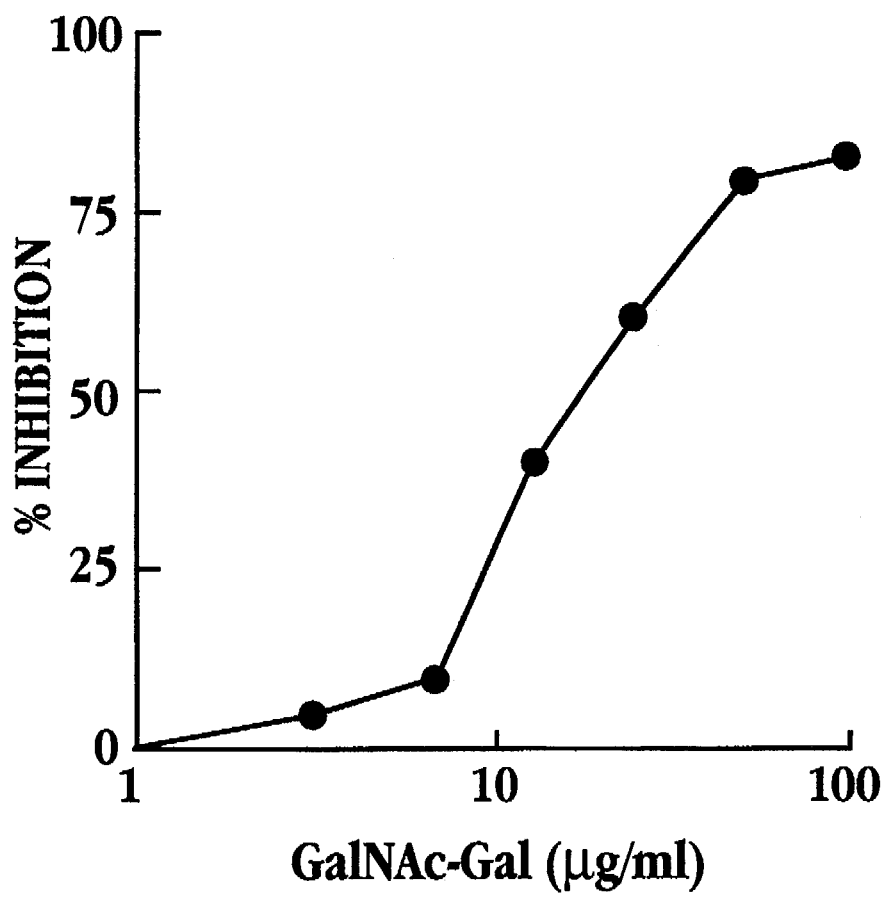

Further experiments were carried out to determine the ability of βGalNAc(1-4)βGal-methylester ("GalNAcGal") to inhibit binding between whole BECs and Candida albicans. FIG. 13C shows the results of experiments in which fungal cells were exposed to increasing concentrations of GalNAcGal, then mixed with BECs. As shown in the figure, GalNAcGal inhibited the fungal cell-BEC interaction in a concentration dependent manner.

IV. Anti-Candida Monoclonal Antibodies

The invention includes, in one aspect, a method of treating systemic infection by Candida albicans. The method includes administering human or humanized antibodies to a subject suffering from such an infection. Preferably, the term "human" antibody refers to an antibody which is substantially human in structure; that is, it derives at least its constant regions from a human antibody. This term includes so-called chimeric antibodies, in which the heavy and light chain constant regions are derived from human genes, while the heavy and light chain variable regions are derived from an immune animal source. The term also includes so-called "humanized" antibodies, in which the heavy and light chain constant regions, as well as the variable region framework regions, are human in origin, and hypervarible regions from an immune source are spliced into the structure. Finally, the term also includes antibodies selected from an combinatorial expression library, such as the immunoglobulin or immunoglobulin expression libraries described by Clackson, et al., Huse et. al., and Marks, et al. The foregoing references are incorporated herein by reference.

Human anti-fimbrial antibodies of the invention may be produced by recombinant methods known in the art. The two methods described herein are based on the discovery that mouse monoclonal antibody Fm16 binds to Candida fimbrial proteins and inhibits Candida binding to epithelial cells. Human antibodies that include variable or hypervariable regions from Fm16, PK99H. or antibodies having substantially the same antigenic specificity as these antibodies, are useful therapeutics for prevention of Candida infection, as discussed below.

Provided with the information concerning the specific immunogenicity of the fimbrial protein preparation and its significance in mediating cell binding, it is now possible, by a variety of methods, to produce human or humanized antibodies useful in the treatment method of the invention. Using the fimbrial protein preparation described herein, it is possible to immunize a non-human primate, test it for the presence of antibodies having substantially the same binding properties as Fm16 antibodies. It is possible to obtain from such animals antibody producing cells for use in producing hybridomas from which mRNA coding for variable regions of anti-fimbrial antibodies can be isolated. Such antibody-producing cells are preferably B-lymphocytes, such as may be isolated from the bone marrow, spleen or from the peripheral circulation.

This section describes the production of antibodies useful in the treatment methods of the invention. In particular, according to the method described below, such production includes the steps of (i) generating in mice monoclonal antibodies specific to Candida fimbriae and effective to inhibit binding of Candida to target epithelial cells, (ii) isolating antibody-producing cells, such as splenic lymphocytes, for production of hybridomas, (iii) cloning from the hybridomas the antibody variable region coding regions, (iv) combining the variable region coding regions with human antibody constant region coding regions in a recombinant cell, and (v) expressing the hybrid human-mouse antibodies.

A. Production of Mouse Anti-Fimbrial monoclonal Antibodies Mouse Anti-*C. albicans* fimbriae monoclonal antibodies can be generated according to standard techniques, using as antigen the fimbrial protein compositions described herein. For purposes of production of monoclonal antibodies, the immunogen can, but need not be a purified protein fraction such as described in Section II above, but will preferably be at least an enriched fimbrial fraction such as the CF, the semi-enriched fimbrial fraction or the EF fraction, described herein.

In experiments carried out support of the present invention, BALB/c female mice were immunized on days 1, 8, 15, 32 and 46 with 10 µg denatured EF fraction containing substantially pure fimbrial protein, as detailed in Example 6. Animals were exsanguinated and the antibody titers of sera were determined according to standard methods by enzyme-linked immunosorbent assays (ELISA), described in Example 7A, using as solid phase coating in the microtiter wells semi-enriched fimbriae at a concentration of 10 µg/ml (0.1 ml/well).

Following the development of high titer antibodies, mouse spleen cells were fused with NS1 mouse myeloma line, according to standard procedures known in the art, as detailed in Example 6. Clones were selected for their ability to synthesize anti-*C. albicans* fimbriae antibodies as determined by ELISA employing EF as the antigens. Positive clones exhibited A405 values in the ELISA assay that were at least twice those of control samples. Western blot analysis (Example 7B) was used to confirm positive results. Positive hybridoma clones were expanded in culture and were frozen and subsequently subcloned twice in semisolid agarose, according to standard procedures. Positive clones, including clone Fm16, are stored in the University of Alberta Microbiology and Infectious Disease Cell Repository, identified by their hybridoma numbers, as referenced herein.

One particular monoclonal antibody, Fm16, from hybridoma Fm16, was selected on the basis of its anti-fimbrial binding activity, described in part B, below. Fm16 produces IgG2ak antibodies, based upon isotyping results obtained with the SBA Clonotyping System II (Southern Biotechnology Associates, Inc., Birmingham, U.S.A.). Ascites tumors were produced by injecting $10^6$ hybridoma cells into pristane-primed BALB/c male mice, according to standard methods (Mischell). Ascites fluid was recovered daily with a 25-gauge needle following the development of an ascites tumor. Typically, 15 ml of ascites fluid was collected over a period of 7 to 10 days.

B. Binding Properties of Monoclonal Antibody Fm16
  1. Binding to antigens

Antigenic specificity of antibodies formed in accordance with the present invention can be determined using one or more of techniques well known in the art. Such techniques are used to screen antibodies for specificity to the fimbrial protein antigen, so that those antibodies having binding specificity that is comparable to that of antibody Fm16 can be selected for use in therapeutic methods of the invention.

ELISA

Antigenic specificity can be determined by ELISA techniques (Example 7A) in which test plate wells are coated with antigen, such as fimbrial protein antigen contained in a semi-enriched fimbriae fraction, or preferably, EF fraction or HPLC purified fimbrial subunit protein, isolated as described above. Test antibodies, such as mouse anti-EF monoclonal antibodies and anti-fimbriae polyclonal sera (obtained from immunized mice that were sacrificed for fusion of mice spleen and NS1 cell line) are then added to each well and binding determined according to techniques well known in the art. In this assay, mouse anti-EF monoclonal antibody Fm16 and polyclonal antibody (sera obtained during the immunization of the BALB/c mice) had high titers for *C. albicans* fimbriae ($10^6$ and $10^5$, respectively). These titers represent the highest dilution of ascites (in the case of Fm16) or serum (in the case of polyclonal antibody) at which reactivity was detected in the ELISA.

Western Blot Analysis. Monoclonal antibodies can be tested for antigenic specificity using Western blot analysis of the immunogen or antigen preparation of interest. According to standard procedures known in the art, the fimbrial antigen preparation is separated on SDS PAGE, then transferred to nitrocellulose. The nitrocellulose strips are then incubated with test antiserum or antibody preparation, then with a species-specific anti-immunoglobulin to which is conjugated a reporter molecule, such as goat anti-mouse heavy- and light-chain IgG-alkaline phosphatase conjugate, for detecting mouse monoclonal antibodies specifically bound to antigen on the nitrocellulose. Comparison of the position on the original gel of the bound protein with known molecular weight or antigen standards is then made, to determine the specificity of the antibody preparation.

In experiments carried out in support of the present invention, fimbriae (CF fraction) were loaded into the wells of a cross-linked running gel, separated by SDS-PAGE and transblotted onto nitrocellulose membrane, as detailed in Example 7B. The blots were then probed with different preparations of anti-fimbrial antibodies, as described below.

Figure 14:
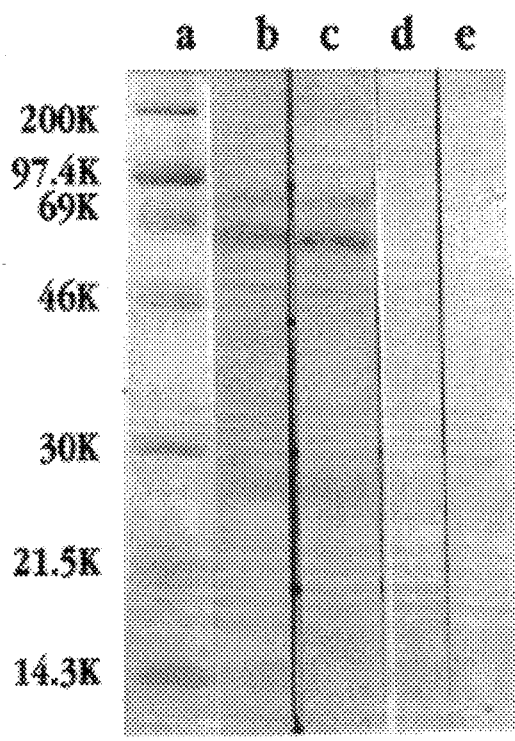
FIG. 14 shows a Western blot of C. albicans CF fimbrial fractions probed with murine ascitic fluid (1:500 dilution) containing antifimbria monoclonal antibody Fm16 (lanes b and c) or with affinity-purified commercial normal mouse IgG (1:500 dilution), where lane a contains standard molecular weight markers.

FIG. 14 shows a Western blot analysis of *C. albicans* CF fraction. Lane a shows molecular weight markers. Fimbriae (CF fraction) in lanes b and c were probed with the murine ascites containing anti-fimbriae monoclonal antibody, Fm16 (diluted 1:500). Lanes d and e were probed with an affinity-purified commercial normal mouse IgG (diluted 1:500) as negative control. A goat anti-mouse IgG-alkaline phosphatase conjugate was used as the secondary antibody. The bands were visualized using nitro blue tetrazolium and 5-bromo-4-chloro-3-indoyl phosphate as the alkaline phosphatase substrates.

As can be observed from the blot presented in FIG. 14, monoclonal antibodies produced by hybridoma Fm16 reacted specifically with a fimbrial protein bands having a molecular weights of 66 kDa and, to a lesser degree, with a band migrating at 69 kDa. It can be appreciated that antibodies useful forming human antibodies of the present invention will also exhibit this binding specificity.

C. Agglutination of fimbrial protein by Fm16 Mab

Agglutination assays (Example 8) were carried out using anti-*C. albicans* monoclonal antibody Fm16 and polyclonal mouse anti-EF antiserum. The results of these assays, summarized in Table 2 below, demonstrate that both antibody preparations bound to antigen present on the surface of fungal cells. Agglutination was demonstrated in a concentration dependent manner consistent with known immunological specificities when either of the anti-fimbrial antibody preparations were added to a whole cell Candida yeast preparation. In contrast, no agglutination was observed when non-immune, normal mouse IgG was used in the assay.

TABLE 2

Agglutination of C. albicans yeast by anti-C. albicans mAb Fm16 and by polyconal anti-Ef antiserum.

| Dilution | Fm16 | Anti-EF anti-serum | Normal mouse IgG |
|---|---|---|---|
| Control (PBS) | — | — | — |
| 1:1 | +++[1] | +++ | — |
| 1:2 | ++++ | ++++ | — |
| 1:4 | +++ | +++ | — |
| 1:8 | ++ | ++ | — |

[1]Agglutination was assessed qualitatively by phase contrast microscopy.

The foregoing experiments demonstrate that the fimbrial protein antigen is present on the surface of the cells and that anti-fimbrial antibodies, particularly those antibodies produced by hybridoma Fm16, were able to bind to this antigen. In accordance with this invention, this binding property is found to indicate ability of the antibody to interfere with Candida fungal cells binding to, and therefore infection of, target human epithelial cells. Accordingly, therapeutic antibodies formed in accordance with the present invention will have the ability to (i) agglutinate Candida cells in vitro, as described above, and to (ii) interfere with binding of Candida cells to target epithelial cells.

D. Inhibition of C. albicans binding to BECs by Fm16 and PK99H Mabs

Studies conducted in support of the invention show that anti-fimbrial antibodies formed in accordance with the invention, i.e., Fm16, have a specificity of binding that is very similar to, if not identical to that of monoclonal antibodies PK99H and PK34C, which were raised against Pseudomonas pili proteins and are described in co-owned U.S. patent application Ser. No. 09/638,492, filed Jan. 4, 1991, which is incorporated herein by reference.

As noted in that '492 application, Pseudomonas pili and Candida fimbria apparently have common binding receptors on epithelial cells and appear to have conserved epitopes on their respective adhesin molecules. This observation is surprising, in view of the distinct dissimilarity at the macromolecular level between the pilin protein subunit, a protein of 144 amino acid residues which forms Pseudomonas pili structures and the highly glycosylated 79 residue peptide which forms the fimbriae of Candida albicans. In addition, conservation of epitopes between other microbial species was noted in the '492 application. In conjunction with the present invention, it has also been found that, like Candida, Pseudomonas binds asialo-GM$_1$ and βGalNAcβGal.

Figure 15:
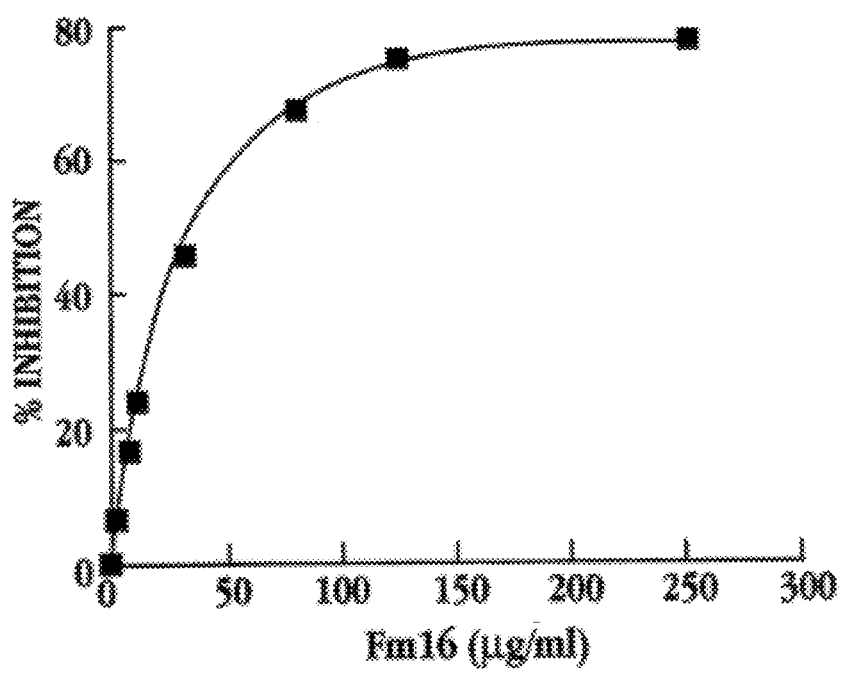
FIG. 15 shows inhibition of fimbrial binding to BECs by monoclonal antibody Fm16.

FIG. 15 shows the percent inhibition of Candida binding to BECs after initial exposure of the fungal cells to the indicated concentration of the Fm16 antibody. Details of the inhibition method are given in Example 9. Significant inhibition of Candida binding to BECs was seen with both antibodies which are specific against Pseudomonas pilin protein C-terminal sequence. Control IgG or diluent had no effect on the Candida-BEC interaction.

According to an important aspect of the present invention, monoclonal antibody Fm16, directed against Candida fimbriae, as well as several other antimicrobial monoclonal antibodies similarly inhibit binding of Candida fimbriae to target epithelial cells. Thus, as shown in the above-referenced '492 application, monoclonal antibodies PK99H and PK34C directed against Pseudomonas pilin, were both effective to inhibit binding of Candida to epithelial cells. Likewise monoclonal antibody 18B-41-13, which was generated against Bordetella pertussis, also binds to Candida fimbriae and exhibits binding properties that are similar to those of Fm16, PK99H and PK34C. These antibodies are all products of hybridomas, identified by the same names and deposited in the University of Alberta Microbiology and Infectious Disease Cell Repository, Alberta, Canada.

E. Forming Human anti-fimbrial monoclonal antibodies

In a preferred embodiment, hybrid antibodies useful in the therapeutic treatment methods of the invention are constructed to include constant regions from human antibodies and to include variable regions from antibodies of the non-human animal species, such as from the mouse described herein. According to methods now established in the art, such hybrid antibodies may be simple chimeric structures, where the entire cloned mouse heavy and light chain variable regions are attached to the constant domains of human heavy and light chains, respectively.

Alternatively, and preferably, such hybrid humanized antibodies are constructed according to a method which recognizes the fact that antibody variable regions consist of relatively constant regions, the framework regions (FRs), and hypervariable regions, the so-called complementarity determining regions (CDRs). By grafting the variable regions of the mouse antibodies into human framework regions (FRs) of the antibodies, the potential for unwanted immune reactions is reduced.

In accordance with the present invention, antibodies useful in the therapeutic methods of the invention will (i) bind Candida fimbria/fimbrial proteins, and (ii) block binding of Candida fimbria/fimbrial proteins to human epithelial cells, in substantially the same manner exhibited by Fm16 antibody. By these criteria, antibodies which would also be useful in this method include PK99H, PK34C, and 18B-41-13, as referenced herein.

Figure 16:
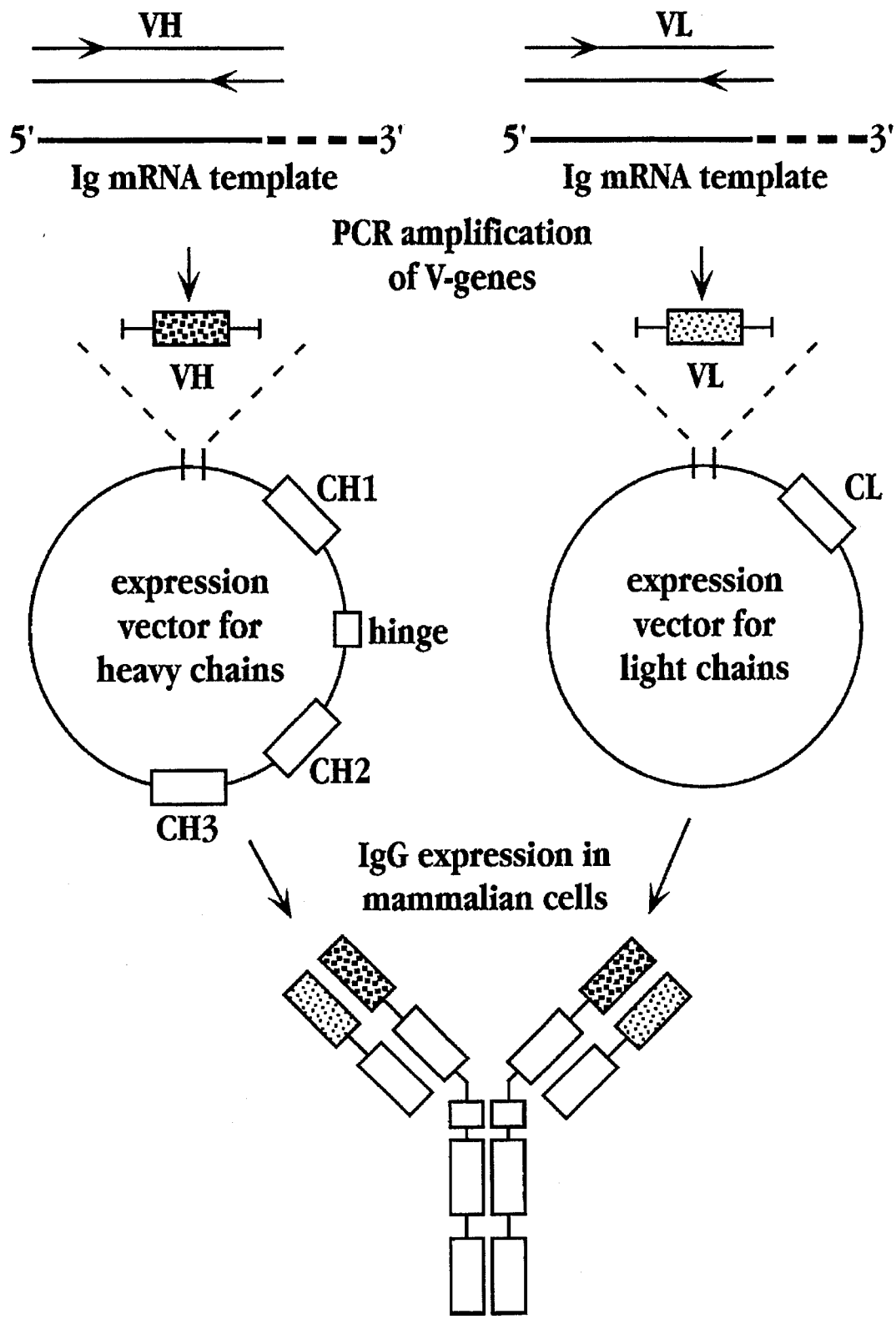
FIG. 16 shows a schematic diagram showing construction of a chimeric human-mouse antibody formed in accordance with the invention.
Figure 17B:
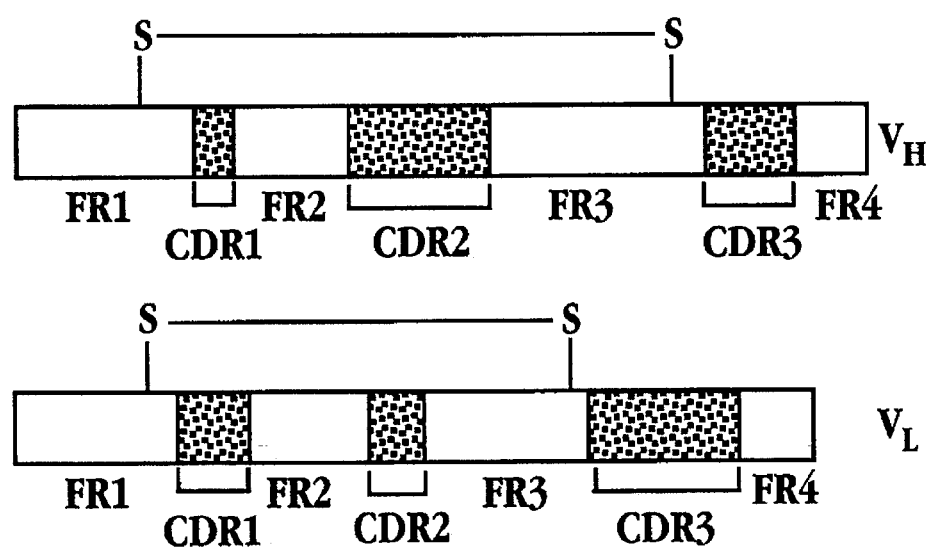

FIGS. 16 and 17 show general constructs of two forms of human recombinant antibodies useful in the present invention. The first type of antibody, shown in FIG. 16 is a so-called chimeric antibody, where the heavy and light chain constant regions are derived from a human source, while the variable regions, indicated as a dark rectangle for the heavy chain variable region ($V_H$) and as a stippled rectangle for the light chain variable region ($V_L$), are derived from a non-human vertebrate source. The second type of antibody, shown in FIG. 17A, is the so-called "humanized" antibody. FIG. 17B is an inset figure to FIG. 17A, showing the framework regions (FR1–FR4) alternating with the hypervariable complement determining regions (CDR1–CDR3) of the heavy and light chain variable regions. In this construct, the variable region framework regions, as well as the constant regions, are derived from a human source.

1. Forming human-mouse Fm 16 chimeric antibodies

FIG. 16 shows a schematic of the process followed to generate chimeric human-mouse antibodies. Generally, as shown, variable regions are cloned from a hybridoma cell line which expresses the hybridoma of interest. Thus, the mouse heavy chain ($V_H$) and light chain ($V_L$) coding regions are cloned and inserted into standard expression vectors for human heavy and light chains. These expression vectors are then transfected into mammalian cells, such as Chinese hamster ovary cells or Sp2/0 cells, which are then able to produce functional humanized antibodies.

In order to produce a humanized Fm16 chimeric antibody, total RNA is prepared from Fm16 hybridoma cells according to a standard guanidinium cesium chloride method (Ausubel). cDNA is prepared from the total RNA, and an oligo dG tail is added to the 3' terminus of the cDNA with terminal deoxynucleotidyl transferase. According to methods well known in the art, H and L chain variable (V) region segments are amplified from the cDNA by polymerase chain reaction (PCR) using primers that (i) anneal to the dG tail and to the gamma or kappa constant regions located 5' to the heavy and light chain variable regions, respectively, and (ii) introduce appropriate restriction sites. The 5'primers are constructed according to known sequences of mouse gamma and kappa constant regions. PCR products are purified according to standard methods, such as by gel purification, digested with restriction endonuclease and ligated into a vector such as pUC18 (Clontech, Palo Alto, Calif.) for DNA sequence analysis (Ausubel). A method of generating such a humanized human-mouse antibody is described in detail by Hakimi et al., which reference is incorporated in its entirety herein by reference.

More specifically, the V-region of the light chain gene is generated by PCR using the Fm16 $V_L$ cDNA as template and 5' and 3' primers, as follows: The 5' primer contains an XbaI site followed by a CCACC ribosome binding site, the ATG initiation codon, and the next 21 nucleotides of the $V_L$ coding region, as determined above. The 3' primer contains the last 18 nucleotides of the VL coding region (noncoding strand) followed by the 13 nucleotides that follow Jκ5 in the mouse genome to include splicing signals and an XbaI site. The PCR product is digested by XbaI, and inserted into the XbaI site of the vector $pV_\kappa$ as described by Co et al. (1992, J. Immunol. 148: 149), which reference is incorporated herein by reference. This vector contains, in addition to the inserted mouse gene, the human Cκ coding region (CHH3, CH2, hinge, CH1), the hCMV promotor and enhancer. The resulting plasmid directs expression of a chimeric Fm16 L chain.

The chimeric H chain gene is generated in a similar manner. The 5' primer contains an XbaI site, ribosome binding site, ATG codon, and the next 15 nucleotides of the $V_H$ coding region. The 3' primer contains a sequence that hybridizes to the last 17 nucleotides of $V_H$, then the 13 nucleotides that follow $J_H3$, and an XbaI site of pVτ1 (Queen, et al., incorporated herein by reference) that contains the human τ1 constant region, an H chain enhancer, and appropriate selectable markers.

A cell line is selected for transfection with the cloned heavy and light chain genes, according to criteria known in the art. One particularly useful is the Sp2/0 cell line (ATCC, Rockville, Md.). About $10^7$ Sp2/0 cells are transfected, by electroporation or by another suitable transfection method. When electroporation is used, about 20 µg each of BamHI linearized L and H chain plasmid DNA is electroporated into the cells using a commercial apparatus, such as a "GENE PULSER" apparatus (BioRad, Richmond, Calif.) at 360 V and 25 microfarad capacitance, following the manufacturer's instructions. Cells from an entire transfection are plated in a 96-well tissue culture plate in nonselective medium (DMEM; GIBCO BRL, Grand Island, N.Y.) supplemented with 10% Fetal Calf Serum (FCS, Hyclone, Logan UT). After a suitable time, generally about 48 hours, spent medium is replaced with selective medium (DMEM with 10% FCS, HT media supplement; Sigma, St. Louis, Mo. supplemented with xanthine, and mycophenolic acid) (Hakimi). Culture medium is assayed for the presence of human IgG according to standard methods by ELISA.

Cells transfected with pVgl based plasmids and producing antibody are further cultured in nonselective medium supplemented with methotrexate in concentrations increasing over time from 50 nM to 10 µM in twofold increments. Typically, cells require two to three days of growth between increases in methotrexate concentration.

1. Forming human-mouse Fm 16 CDR grafted antibodies

A preferred method for humanizing mouse monoclonal antibodies in accordance with the present invention is the CDR grafting method referred to above, and shown schematically in FIG. 17. Human antibodies formed according to this method exhibit reduced immunogenicity when administered to humans by virtue of increased proportion of human-derived immunoglobulin. FIG. 17A shows a schematic of a CDR grafted antibody, with light and heavy chain constant regions coded for by human genomic sequences (diagonal lined regions). The variable regions of the antibody are shown in expanded view in FIG. 17B. Here, the hypervariable CDR regions (CDR 1-3) are derived from mouse, while the framework regions (FR 1-4) are derived from human sources.

In this method, which is now well known in the art and has been described in detail by Sato et al. (incorporated herein by reference in its entirety), the complementarity determining regions (CDRs) from the variable regions of the mouse Mab are grafted into human variable regions to create "reshaped" human variable regions. The only portions of the final reshaped human antibody derived from non-human protein sequence are the CDRs. CDRs are highly variable amino acid sequences.

Total RNA is prepared from the hybridoma cells according to a standard guanidinium cesium chloride method, as described for production of chimeric antibodies. First-strand cDNA synthesis is carried out using 5 µg of total RNA. cDNAs encoding $V_L$ and $V_H$ regions are amplified using PCR primers designed for rapidly cloning entire mouse antibody variable regions (Jones and Bendig, 1991, incorporated herein by reference). After cloning the cDNAs into pUC19 vectors (Clontech, Palo Alto, Calif.), the DNA sequences were determined. The amino acid sequences of the $V_L$ and $V_H$ regions were compared, first to the sequences of all known mouse and human antibody variable regions as found in Leeds (OWL Composite Protein Sequence Database, University of Leeds, U.K.), and second to the sequences of immunoglobulin variable regions present in the Brookhaven database of protein structures.

Using PCR methods, the cDNAs coding for the mouse Fm16 $V_L$ and $V_H$ regions are modified to have HindIII sites and Kozak sequences at the 5' sides, and BamHI sites and splice donor sequences at the 3' and sides. The V regions are then linked to the genes encoding human kappa or human gamma-1 constant regions as present in the expression vectors.

The reshaped human $V_H$ region may be designed based on the consensus amino acid sequence for human $V_H$ regions belonging to subgroup I(HSG-I). This can be constructed by the CDR-grafting method described above. A plasmid DNA, pUC-RVh-425a, which has FRs based on HSG-I (Kettleborough, et al., 1991), is used as the template DNA. The final PCR product is digested with HindIII and BamHI and subcloned into a pUC19 vector. After DNA sequencing, the BamHI-HindIII DNA fragments encoding the sequence is excised from the plasmid DNA and then subcloned into an HEF expression vector.

The light and heavy chain expression vectors are then co-transfected into appropriate cells, such as COS cells, according to the methods described above for the chimeric antibody construction, and preferably by electroporation. Equal amounts of each plasmid DNA (10 µg) are added to 0.8 ml of cells suspended in PBS at a concentration of about $10^7$ ml$^{-1}$. A pulse is delivered in accordance with standard methods using a commercial electroporation apparatus. After a 10 minute recovery period at room temperature, the electroporated COS cells are added DMEM media containing 10% gamma globulin-free fetal calf serum (GIBCO, Ground Island, N.Y.). After 72 hours incubation, the medium is collected, centrifuged to remove cellular debris, and applied to a Protein A agarose column (such as "AFFI-GEL PROTEIN A MAPSII KIT", BioRad, Richmond, Calif.) equilibrated with binding buffer. After washing with binding buffer, antibodies are eluted with elution buffer. The elute is concentrated and the antibodies are transferred to an appropriate excipient or medium, such as phosphate buffered PBS, for use in producing a therapeutic composition.

V. Fimbriae Polypeptides

In another aspect, the invention includes purified polypeptide fragments from the isolated C. albicans fimbrial protein. The polypeptides are relatively short, typically less than about 20 amino acids, and are characterized by specific binding affinity for either the monoclonal antibody produced by mouse hybridoma cell line Fm16 or cell line PK99H, or for βGalNac(1-4)βGal moieties.

The peptides may be prepared by solid-phase synthetic methods, or by recombinant DNA methods. In the former case, known-sequence fragments of the fimbriae polypeptide, preferably overlapping sequences or 10–20 amino acids in length, are prepared by standard solid-phase peptide procedures. After synthesis on the solid phase, the peptides are released to form a solution phase peptide.

Identification of high-affinity peptides can be carried out by the fimbrial protein binding methods detailed above, where binding to one of the monoclonal antibodies or to βGalNac(1-4)βGal is assayed.

Peptides showing high binding affinity, as measured, for example, by the ability of the peptides to compete with fimbrial protein for binding to the antibody or to GNG, are then identified. The identified peptides may be further screened for their ability to block fibrial protein binding to BECs and for their ability to block C. albicans binding to BECs.

The peptides may be useful as immunization reagents for producing immunity against Candida infection, and as diagnostic reagents for detecting the presence of Candida-specific antibodies in infected individuals.

VI. Treatment Method

This section describes a method for treating candidiasis from C. albicans infection. In one general embodiment, the method is used to treat localized infection, typically oral or vaginal infection, and employs the βGalNac(1-4)βGal composition described above. In a second general embodiment, the method is employed to treat disseminated, or systemic infection, and uses the antibody composition described above.

A. Treating Localized Infection

Binding studies discussed above show that βGalNa-c(1-4)βGal is effective in blocking C. albicans binding to epithelial cells. The present method exploits this finding, in a method of inhibiting C. albicans infection by inhibiting binding of the infectious agent to target epithelial cells.

Local infection of the oral or vaginal mucosa is treated, in accordance with the method, by topical application of βGalNac(1-4)βGal, preferably in the form of a βGalNac(1-4)βGal conjugate of the type described above. For oral delivery, the composition may take the form of a wash or cream that can be applied, e.g., by swab or mouth rinsing at periodic intervals. Alternatively, the composition may be incorporated into a buccal suppository for release from the gum region over an extended period. In another embodiment, the composition may be incorporated into a slow-release tablet or oral insert, or into gum. Methods for forming oral delivery creams or devices of this type, for topical administration of incorporated composition into the oral cavity are well known.

For vaginal delivery, the composition may be administered in cream form, or by vaginal suppository or insert, according to known drug-delivery methods.

The composition is administered in a a pharmaceutically effective amount, that is, an amount effect to inhibit C. albicans binding to oral or vaginal mucosal cells. As seen from the studies on inhibition of C. albicans binding to BEC's, the administering is preferably effective to produce a level of a multivalent βGalNa-c(1-4)βGal conjugate of at least about 10 µg/ml, and preferably between about 10 and 100 µg/ml, over an extended period, e.g., 30–120 minutes. For administration by monovalent βGalNAc(1-4)βGal, the dose levels should be substantially higher, e.g., in the range between about 50 to 500 µg/ml.

Administering the composition is continued until a desired reduction of infection is achieved, as monitored, for example, by the reduction of fungal organisms collected by oral or vaginal swab, and/or by an observed change in the symptomatic condition of the patient.

Where the composition is employed for prophylactic purposes in an individual who may be at risk for oral or vaginal infection, the same modes of composition administration may be employed. In particular, a βGalNac(1-4)βGal composition, at the dosage levels indicated above, is administered for a period of at least a few days, or until the risk of infection has passed.

B. Systemic or Disseminated Infection

In another general aspect, the infection includes treating a disseminated or systemic C. albicans infection by parenteral administration of an anti-fimbriae antibody, preferably a human or humanized antibody of the type described above. The treatment method is based on the discovery herein that anti-fimbriae antibodies of the type described above are effective in blocking fimbriae and Candida binding to epithelial cells, The antibody is administered typically in a physiological saline solution, at an pharmaceutically effective dose, i.e., a dose effective to inhibit fungal cell levels in the bloodstream or at an organ site. Administration may be by intravenous, intramuscular, subcutaneous or other parenteral route.

An effective dose level of antibodies can be determined from a suitable animal model system in which anti-fimbriae antibodies are screened for their ability to prevent or treat systemic infection by C. albicans. A preferred dose is between 0.1 to 2 mg/kg body weight.

The dose may be confirmed by animal studies, such as studies on Candida-infected mice. Here mice infected by injection with C. albicans are treated with repeated doses of antibody, in amounts ranging from 0.1 to 2.0 mg antibody/kg body weight, at days 2, 4, 6, 8 post-infection. The animals are then monitored at the end of this period for systemic fungal infection, as measured by fungal colony forming units in a given volume of blood. The dosage range effective to reduce infection is then taken as the range for initial clinical trials on the antibody.

To monitor therapy, blood samples collected during treatment of the patient can be monitored for colony forming units, and/or changes in the symptomatic condition of the patient.

The following examples illustrate, but in no way are intended to limit the present invention.

Materials and Methods

C. albicans strain #40 was obtained from the trachea of an intubated intensive care unit patient at Toronto General Hospital. The isolate has been maintained at −70° C. in 40% glycerol containing 3% trisodium citrate following the initial isolation and microbiological characterization of the isolate. The isolate was subsequently recovered on Sabouraud-dextrose (SAB) agar (GIBCO) at 37° C. for 18 hours. *C. albicans* was then recultured on SAB agar plates for 18 hr at 37° C. and harvested in 3 ml of 10 mM phosphate buffer saline (PBS) pH 7.2 and utilized to inoculate trays (30 cm×22 cm) of SAB agar which were then incubated for 5 days at 37° C. before cells were harvested.

EXAMPLE 1

Purification of *C. albicans* fimbriae

Fimbriae were purified from yeast phase of *C. albicans*. *C. albicans* cells were harvested from the agar surface by gentle scraping with a bent glass rod. Harvested cells were suspended in a minimal volume (50 ml/tray) of Preparation Buffer (10 mM sodium phosphate saline pH 7.2, containing 1 mM $CaCl_2$ and 1 mM phenylmethylsulfonyl fluoride). Harvested cells were washed three times with 500 ml of Preparation Buffer by centrifugation (12,000×g for 20 min at 4° C.). Fimbriae were sheared from the cell surface by gentle homogenization (4×45 second cycles) using a Brinkmann Homogenizer. The cells were removed by centrifugation (12,000×g for 20 min) and by subsequent filtration of the supernatant through a 0.45 μm filter (Millex-PF, Millipore). The supernatant was concentrated approximately 10-fold with polyethyleneglycol, PEG (M.W. 8,000). The concentrated fimbriae preparation was dialyzed overnight at 4° C. against Preparation Buffer. This material was termed crude fimbriae (CF). The CF preparation was fractionated by size-exclusion high performance liquid chromatography using an isocratic gradient (flow rate=0.5 ml/min; column= Waters Protein-PAK 300 SW 10 μm) with Preparation Buffer as the solvent. The material that was eluted in the void volume was collected, concentrated with PEG and dialyzed against Preparation Buffer. This material was termed semi-enriched fimbriae and was rechromatographed under identical conditions. The peak which corresponded with the void volume of the column was again collected, concentrated and dialyzed against Preparation Buffer. This fraction was termed enriched fimbriae (EF).

A typical fimbriae preparation from 200 g wet weight of *C. albicans* yielded about 70 mg of crude fimbriae (CF), which then yielded 5 mg of enriched fimbriae (EF).

Protein concentrations of CF and EF were determined using a bicinchoninic acid (BCA) protein assay (Pierce) described by Smith et al. with bovine serum albumin (BSA) employed as the protein standard to generate a standard curve.

EXAMPLE 2

Purification of Adhesin Protein from Fimbriae

A. Isolation of purified Fimbrial Protein

Figure 1B:
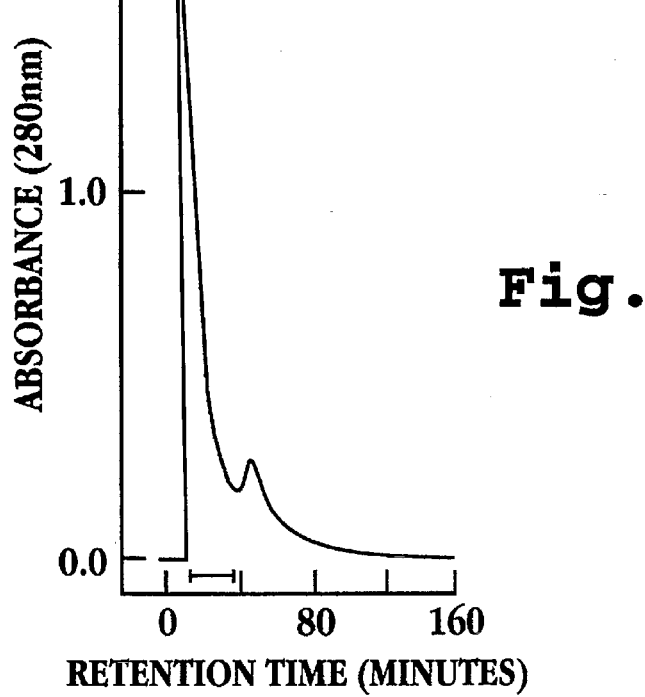

Fimbriae were removed from washed cells by shearing, separated from cells by centrifugation and filtration and then subjected to HPLC size-exclusion chromatography (SEC) as detailed in Example 1. The fimbriae eluted as two peaks (the first peak eluting at the void volume of the column) as illustrated in FIG. 1A. Fimbriae were mainly associated with the first peak, as determined by SDS-PAGE and electron microscopy, carried out according to the methods detailed in Example 3. The first peak was collected and rechromatographed under identical conditions with the fimbriae eluting at the void volume of the column (FIG. 1B). The presence of the second peak on the rechromatography profile indicated that some of the fimbrial preparations were depolymerized and/or deglycosylated during the purification process.

CF and EF preparations obtained as described above were analyzed by SDS-PAGE, as described in Example 3. FIG. 2 shows a protein-stained gel containing fractions from CF (lanes a and b), semi-enriched fimbriae eluted from first HPLC fractionation (lanes c and d) and EF (lanes e and f). The enriched fimbriae (EF) preparation contained almost pure fimbriae (FIG. 2, lanes a and b). The molecular weight of the purified fimbrial subunit present in the EF fraction was approximately 66 kDa.

To purify the fimbrial protein, gel slices containing the 66 kDa protein were cut out of the gel. The gel slices were washed (2×5 min) with elution buffer (20 mM ammonium bicarbonate) by gently shaking at 50 rpm on a Gyrotory shaker model G2 (New Brunswick Scientific Co.) for 30 min at room temperature. The gel slices were put into dialysis tubing (M.W. cut-off of 6000 to 8000) and suspended in water. The proteins were electroeluted from the gel slices in 20 mM ammonium bicarbonate using an electroelution apparatus (Schleicher & Scheull Elutrap™) by applying a constant voltage of 200 V for 5 hours or 80 V overnight. The eluate was collected and dialyzed against deionized water.

The eluted protein fraction was further purified by reversed-phase HPLC (Aquapore $C_4$column 100×4.6 mm, 7 μm internal diameter) using a linear AB gradient (where solvent A is 0.05% aqueous trifluoroacetic acid [TFA] and solvent B is 0.05% TFA in acetonitrile) of 2% B/min gradient at a flow rate of 1 ml/min. FIG. 4 shows a chromatograph of this separation. The eluate containing the peak was collected and lyophilized.

B. Amino acid composition

Amino acid analysis of Candida fimbrial protein was carried out on the protein fraction purified by reversed-phase chromatography, as described in Part A.

A small amount of the lyophilized fraction was hydrolyzed in a glass tube with 200 μl of 6N HCl, containing 0.1% (w/v) phenol at 110° C. for 24 hours in vacuo. The acid from the hydrolysate was removed by evaporation, resuspended in citrate buffer pH 2.2 and the amino acid content was analyzed with a Beckman Model 6300 amino acid analyzer. No attempt was made to analyze for total ½ Cys or Trp, nor were the values for Ser and Thr corrected to take into account losses during hydrolysis. Table 2-1 shows the amino acid composition as number of residues/fimbrial subunit determined for *C. albicans* strain 40, using this method.

C. Carbohydrate composition

A phenol-sulfuric acid carbohydrate assay described by Dubois et al. was used to determine the amount of carbohydrate present in the EF preparation. EF was diluted 1:10 with 2N $H_2SO_4$. Diluted EF (0.5 ml) was added to 0.5 ml of a 5% solution of aqueous phenol and 2.5 ml of $H_2SO_4$ reagent (2.5 g hydrazine sulfate in 1 L of concentrated sulfuric acid) and mixed vigorously before incubation in the dark for 1 h at room temperature. The absorbance at 490 nm of the reaction mixture was recorded. D-mannose (Sigma) was dissolved in 2N $H_2SO_4$ and employed as a standard (0 to 100 μg/ml).

Based on the known amount of EF used for the carbohydrate analysis, both the protein and carbohydrate content in the *C. albicans* fimbriae were used to determine the ratio of carbohyrate and protein.

The carbohydrate composition of the EF was investigated as described by Bryn and Jantzen (2, 3). Briefly, lyophilized carbohydrate samples were methanolyzed with dry 2M HCl methanol for 16 hours at 85° C. The derivatization mixture (2 µl) was used directly. Samples were analyzed with a Varian Vista 6000 equipped with a Varian CDS 401 data station and a flame ionization detector, and employed a J & W DB-5 (95% methyl-, 5% phenylpolysiloxane) 30 cm long×0.25 mm internal diameter column using helium carrier at a flow rate of 1 ml/min. The column was held isothermally for the initial 4 min at 90° C. then rose at 8° C./min to a maximum of 270° C. Authentic carbohydrate samples (Sigma) were derivatized and utilized as a standards.

EXAMPLE 3

Physical properties of purified fimbriae

A. Molecular weight

Sodium dodecyl sulfate-polyacrylamide gel (SDS-PAGE) was performed with 12.5% acrylamide gels in a mini-gel apparatus (Mini-protein® II Dual Slab Cell, Bio-Rad) as described by Laemmli (31). Samples were electrophoresed for 50 min at a constant voltage of 200 V with a power supply model 1420A (BioRad Laboratories). Gels were stained with Coomassie blue (R-250, Bio-Rad) or with silver stain.

B. Electron microscopy

Fimbriae were diluted 1:100 with 10 mM sodium phosphate buffer pH 7.2. A 20 µl drop of diluted fimbriae solution was placed on a freshly prepared carbon/formvar coated 3 mm 200 mesh copper electron microscope grid (Fisher Scientific). The grid was blotted with Whatman #1 filter paper, then negatively stained with 1% (w/v) phosphotungstic acid at a pH 7.0 for 10 seconds. The stain was removed by blotting and the sample was examined with a Philips model 410 transmission electron microscope operating at an accelerating potential of 80 kV. Micrographs were recorded on Kodak electron microscope film #4489.

Scanning electron micrographs of fimbriae of yeast phase C. albicans bound to human BECs were obtained according to the methods of Murakami et al. (39). Specimens (3 ml) were fixed with a 2.5% (v/v) glutaraldehyde (J. B. EM Services Inc., Point Claire, Dorval Quebec) in 0.1M phosphate buffer pH 7.3 and incubated overnight at 4° C. Samples were aliquoted in 1.5 ml eppendorf tubes centrifuged at 120 rpm for 10 minutes and washed 3×20 min with 1.0 ml phosphate buffer pH 7.3. Samples were post-fixed in 2% (w/v) osmium tetroxide in 0.1M phosphate buffer pH7.3 for 1 hour. The cells were washed by centrifugation as described above. Specimens were then resuspended in 1.0% (w/v) tannic acid in distilled water and incubated for 30 minutes at room temperature. The solution was removed by aspiration and the cells were washed with water and then resuspended in 2% (w/v) aqueous osmium tetroxide for 1 hour and then washed with water. Specimens were then dehydrated in a graded series of ethanol to 100%. Samples were critical point dried and subsequently salted onto a standard Cambridge scanning electron microscope stub precoated with double-sided adhesive tape. Specimens were then directly examined in a Hitachi S 4000 field emission scanning electron microscope at an accelerating potential of 2.5 kV.

EXAMPLE 4

Binding of Fimbriae and Fungal Cells to Epithelial Cells

A. Direct Fimbrial Binding Assay

Human buccal epithelial cells (BECs) were collected from 10 healthy, non-smoking male volunteers by gentle scraping of the buccal mucosal surface with wooden applicator sticks. These sticks were then agitated in 40 ml of PBS pH 7.2 to remove the BECs. BECs were washed 3×10 min with 10 ml of PBS by centrifugation at 2,000×g. Cell clumps were removed by filtration through a 70 µm nylon mesh (Spectrum, Cole-Parmer). The cell concentration was determined directly with a hemocytometer and BECs were resuspended in PBS to a concentration of $2.0 \times 10^5$ BECs/ml.

The fimbrial adherence assay was performed using a Manifold filtration apparatus equipped with individual vacuum stopcocks (Model FH 225V, Hoefer Scientific Instruments). Polycarbonate filters, 12 µm pore size (Nucleopore Costar Corp.), were pre-incubated overnight at 4° C. with 50 ml of PBS pH 7.2, containing 0.45% (v/v) Tween 20. The pretreated filters were placed into each chamber and washed with 2.5 ml of PBS. 1 ml containing $2.0 \times 10^5$ BECs in PBS was added to each chamber. Enriched fimbriae (100 µl/chamber, ranging from 0 to 80 µg fimbriae protein/ml) in PBS containing 0.05% (v/v) Tween-20 was added to each chamber and incubated with the BECs for 1.5 hours at room temperature. Unbound fimbriae were removed with washes of 2.5 ml of PBS. Mouse anti-C. albicans fimbriae monoclonal antibody (ascites fluid diluted 1:3000 with PBS) was added to the BECs (1.2 ml/chamber) and incubated for 1.5 hour at room temperature. BECs were washed five times with 2.5 ml of PBS. Goat anti-mouse IgG(H+L)-peroxidase conjugates (Jackson Laboratories) diluted 1:5000 with PBS was added (1.0 ml/chamber) and incubated for another hour at room temperature. The cells were then washed seven times with 2.5 ml/chamber of PBS. The polycarbonate filters containing BECs were removed from the filtration manifold and placed into glass scintillation vials. The horseradish peroxidase substrate solution (ABTS) was added to each vial (1 ml/vial) and incubated for 30 min at room temperature on a shaker at 100 rpm. The reaction was stopped by the addition of 4 mM sodium azide (200 µl/vial). The substrate solution was pipetted into Eppendorf tubes and centrifuged at 5,000 g for 3 minutes. Aliquots of the supernatants were pipetted into microtiter wells (200 µl/well) and the resulting absorbance at 405 nm was recorded with a Titertek Multiskan Plus microplate recorder.

B. Inhibition of C. albicans binding to BECs

C. albicans cells were radiolabelled as previously described by McEachran and Irvin (35, 48), incorporated herein by reference. A loopful of culture from Sabouraud-dextrose agar (GIBCO) was used as a source of inoculum for 10 ml of M9 medium supplemented with 0.4% (w/v) glucose. Cultures were incubated at 25° C. for 12 hours with 150 rpm agitation in G25 Gyrotory shaker (New Brunswick Scientific Co.). Cultures were supplemented with 5 µCi/ml of [$^{35}$S]-L-methionine (New England Nuclear, Boston, Mass.) after 10 hours of incubation. Cells were harvested by centrifugation (12,000×g for 10 min) and washed 3 times with 10 ml of PBS pH 7.2 to remove unincorporated methionine. Washed cells were resuspended in PBS. No clumping was observed during the assay. The amount of [$^{35}$S]-L-methionine incorporated by the C. albicans cells was determined by filtering 1.0 ml of a 1:100 dilution of washed C. albicans culture through a 0.2 µm polycarbonate filter (Nucleopore Corp., Pleasanton, Calif.) in triplicate, washing with 15 ml of PBS, and placing the filter in scintillation vials with 5.0 ml of Aquasol (New England Nuclear, Massachusettes). The counts per minute were determined with a Beckman LS-150 liquid-scintillation counter. The specific activity of [$^{35}$S]-C. albicans cells was generally 0.2 cpm/CFU and this remained stably associated with the C. albicans cells throughout the assay.

BECs (0.5 ml) were preincubated with EF at varying concentrations (from 0 to 18 μg protein/ml) in polystyrene tubes at 37° C. for 1 hour (final concentrations: $2.0 \times 10^5$ BECs/ml). An equal volume of radio-labelled yeast suspended in PBS pH 7.2 was added to the BECs and incubated at 37° C. for 2 hours, shaking at 300 rpm. Triplicate aliquots were removed after the assay and filtered through 12 μm polycarbonate filters pretreated with 3% (w/v) BSA in PBS. BECs were washed with 15 ml of PBS. The filters were then placed in scintillation vials and the cpms were determined as described above. Yeast binding to BECs was corrected for nonspecific binding of yeast to the 12.0 μm filter (nonspecific binding was generally less than 15% of the experimental value). The BEC concentration was determined at the end of the assay to correct for cells lost during incubation.

In a similar manner, experiments were carried out testing the ability of βGalNac(1-4)βGal to inhibit binding of *C. albicans* to BECs. Results of these tests are described in the text and shown in FIG. 13C. Total and viable cell counts were performed before and after the adhesion assay. Total cell counts were determined using a hemocytometer. Viable counts were determined by serially diluting *C. albicans* in PBS pH 7.2 and plating appropriate dilutions on SAB agar which were incubated at 37° C. until visible and countable colonies formed (usually 24 to 48 hours).

EXAMPLE 5

Binding of Candida fimbriae to Glycosphingolipids

A. Thin-layer Chromatography Plate Binding Assay

The thin-layer chromatography (TLC) plate binding assay was performed as described by Baker et al. (1) with minor modifications. Aluminum-backed silica gel Si60 high performance TLC plates (Merck Kieselgel Si60, no fluorescence indicator, E. Merck, Darmstadt, Germany) were cut to produce 8×2.5 cm plates which were chromatographed with 100% methanol to the top of the plate to remove impurities and the plates were air dried. Glycosphingolipids (GSLs) (10 μg of each GSL) were loaded 1.0 cm above the base of the plate. The following glycosphingolipids purchased from Sigma Co. (St. Louis, Mo.) were used: mono-sialoganglioside (M-GM$_1$), asialoganglioside GM$_1$ (asialo-GM$_1$), asialoganglioside GM$_2$ (asialo-GM$_2$), lactosylcerebroside (LCS), ceramide trihexoside (CTH). GSLs were separated on the TLC plates in chloroform-methanol-water (65:35:8, v/v/v) and air dried. One set of plates was sprayed with 10% sulphuric acid in ethanol and heated at 100°–150° C. for 5–10 min to char the GSLs for visual detection, and the other set was used for the fimbrial binding assay. The four corners of the plate were bent to 90° and the remainder of the assay was done with the TLC plates inverted in all solutions and at room temperature in an incubator shaker (model G25 Gyroshaker, New Brunswick Scientific, New Jersey, U.S.A.) at 20 rpm agitation. The TLC plate was blocked with 50 mM tris-hydroxy-methyl aminomethane pH 7.5 containing 150 mM NaCl (TBS), 0.25% (w/v) gelatin, 3% (w/v) BSA, 5 mM EDTA and 0.05% (v/v) Nonidet P40 in a glass petri dish for 2 hr at room temperature. The blocking solution was aspirated and 10 ml of EF (100 μg EF/ml in 100 mM TBS, pH 7.5) was then added. The fimbriae were allowed to bind to GSLs for 2 hours at room temperature. The plates were gently washed (2×5 min) with 10 ml of 100 mM TBS containing 0.1% (v/v) Tween 20 (TBST). The murine anti-EF monoclonal antibody, Fm16, was diluted 1:200 with TBST and 10 ml was added to the TLC plates. The solution was incubated for 1 hour at room temperature. Unbound antibodies were removed by washing the plates with 10 ml of TBST (2×5 min). The plate was then incubated with 10 ml of goat anti-mouse immunoglobulin G alkaline phosphatase conjugate (Jackson Laboratories) diluted 1:5,000 with TBST for 1 hour at room temperature. The plates were washed (2×5 min.) with 10 ml of TBST. The alkaline phosphatase activity was localized with Nitro Blue Tetrazolium chloride (NBT) and 5-bromo-4-chloro-3-indolyl phosphate (BCIP) dissolved in 100 mM Tris buffer, pH 9.5 containing 100 mM NaCl and 5 mM MgCl$_2$. Color development was quenched by rinsing the TLC plate with deionized water and submerging the plate into a 150 mM EDTA solution pH 8.0 for 3–5 min. The plates were air dried, stored in plastic in the dark until they were photographed.

B. Plate binding assay

Polystyrene microtiter plate wells (Nunc) were coated with asialo-GM$_1$ or ceramide trihexoside (CTH) (Sigma Chem. Co., St. Louis, Mo.). Aliquots of the GSLs (5 μg/ml resuspended in methanol) were added into the wells (100 μl/well) and the plates were incubated overnight at 4° C. The wells were washed three times with 250 μl/well of 10 mM phosphate buffered saline pH 7.4 containing 150 mM NaCl (PBS) supplemented with 0.05% (w/v) bovine serum albumin (Buffer A). Excess binding sites were blocked by the addition of 200 μl/well of 5% (w/v) BSA in PBS pH 7.4 and incubation at 37° C. for 1 hour. Wells were washed three times with 250 μl/well of buffer A. Enriched fimbriae ranging from 0 to 40 μg protein/ml in Buffer A were added to the wells (100 μl/well) and incubated for 2 hour at 37 ° C. Aliquots of mouse anti-EF monoclonal antibodies, Fm16 (diluted 1:500), was added to each well (100 μl) and incubated at 37° C. for 2 hours. Wells were washed 5 times with 250 μl/well of Buffer A. Antibody binding to EF was assessed by the addition of a goat anti-mouse heavy and light chain [IgG(H+L)] immunoglobulin G-peroxidase conjugates (Jackson Laboratories) to each well (100 μl/well) and incubated for 1 hour at 37° C. The wells were washed 5 times with 250 μl/well of Buffer A and a substrate solution containing 1 mM 2,2'-azido-di-[3-ethylbenzthiazoline sulfonic acid] (ABTS) in 10 mM sodium citrate buffer (pH 4.2) containing 0.03% (v/v) hydrogen peroxide was added (125 μl/well). The reaction was stopped by an addition of 125 μl/well of 4 mM sodium azide and the absorbance at 405 nm was recorded.

Inhibition of binding of Candida fimbrial binding was carried out as described above, except that *C. albicans* fimbriae were preincubated with asialo-GM$_1$ and CTH, respectively, for 1 hour at 37° C. prior to their addition into the wells. A fixed concentration of EF (50 μg/ml) was incubated with varying GSL concentrations (0 to 15 μg/ml) in these assays. The remaining of the protocols were as described above with the direct binding assays.

EXAMPLE 6

Production of Mouse Mabs

Anti-*C. albicans* fimbriae monoclonal antibodies, Fm16 were produced with a hybridoma technique previously employed to obtain *P. aeruginosa* pili monoclonal antibodies (10). BALB/c female mice (Charles River Breeding Laboratories Inc.) were immunized on days 1, 8, 15, 32 and 46 with 10 μg EF in a 1% (w/v) Al(OH)$_3$. The EF were first denatured by boiling in a 1% (w/v) SDS and 1 mM β-mercaptoethanol. Animals were exsanguinated and the antibody titers were determined by enzyme-linked immunosorbent assays (ELISA) with the semi-enriched fimbriae (10 μg/ml) as the coating antigens in the microtiter wells (100 μl/well).

Following the development of high titer antibodies, 3 mice were sacrificed and their spleens removed aseptically. The mouse myeloma used for the production of hybridoma clones was NS1. The NS1 cell line was cultured in high-glucose Dulbecco modified Eagle medium supplemented with 2 mM L-glutamine and 10% (v/v) fetal calf serum (GIBCO Laboratories) at 37° C. in the presence of 5% $CO_2$. Cells were passed every 48 h at a split ratio of 1:5 or 1:4. Production and selection of hybridomas were carried out as described by Irvin and Ceri (23), except that the medium was not supplemented with β-mercaptoethanol. Clones were selected for their ability to synthesize anti-*C. albicans* fimbriae antibodies as determined by ELISA employing EF as the antigens. Positive clones had A405 values that were double or greater than control levels. These results were confirmed by Western blots. Positive hybridoma clones were scaled up into 5 ml Dulbecco modified Eagle medium supplemented with 20% (v/v) fetal calf serum, 2 mM L-glutamine, hypoxanthine, aminopterin, and thymidine. Clones were frozen and subsequently, subcloned twice in semisolid agarose (25, 26). One particular monoclonal antibody, Fm16, was chosen for further analysis. Fm16 is an IgG2ak based upon isotyping results obtained with the SBA Clonotyping System II (Southern Biotechnology Associates, Inc., Birmingham, U.S.A.) Ascites tumors were produced by injecting $10^6$ hybridoma cells into pristine-primed BALB/c male mice (30). Ascites fluid was recovered daily with a 25-gauge needle following the development of an ascites tumor. Typically, 15 ml of ascites fluid was collected over a period of 7 to 10 days.

EXAMPLE 7

Screening of Antibodies

A. ELISA

Polystyrene microtiter wells (Nunc) were coated with semi-enriched fimbriae (10 µg/ml in 0.01M carbonate buffer, pH 9.5) by an overnight incubation at 4° C. The wells were washed three times (250 µl/well) with PBS pH 7.4 supplemented with 0.05% (w/v) bovine serum albumin (Buffer A). Excess binding sites were blocked by incubation at 37° C. for 1 hour with 5% (w/v) BSA in PBS pH 7.4. Wells were washed three times with 250 µl/well of Buffer A. Aliquots (100 µl/well) of serially diluted mouse anti-EF monoclonal antibodies and anti-fimbriae polyclonal sera (obtained from immunized mice that were sacrificed for fusion of mice spleen and NS1 cell line) were added to each well and incubated at 37° C. for 2 hours. A rabbit polyclonal antiserum directed against another pathogen was also tested as negative control. Wells were washed 5 times with 250 µl/well of Buffer A. Antibody binding to EF was assessed by adding 100 µl/well (1:5,000) goat anti-mouse or goat anti-rabbit heavy and light chain [IgG(H+L)] immunoglobulin G-peroxidase conjugates (Jackson Laboratories). Following a 1 hour incubation at 37° C., the wells were washed 5 times with 250 µl/well of Buffer A and a substrate solution containing 1 mM 2,2'-azido-di-[3-ethylbenzthiazoline sulfonic acid] (ABTS) in 10 mM sodium citrate buffer pH 4.2, containing 0.03% (v/v) hydrogen peroxide was added (125 µl/well). The reaction was stopped by the addition of 4 mM sodium azide (125 µl/well) and the absorbance at 405 nm was recorded.

The apparent affinity of the antibody for the competitor was determined as described by Nieto et al. (1984) following determination of the concentration of competitor that would give 50% inhibition of antibody binding to antigen.

B. Western Blot

Proteins on the separated on SDS-PAGE gel as described in Example 2 were transferred to nitrocellulose membrane using the protocol of Towbin et al. (52) with a Mini Trans-Blot Electrophoretic Transfer Cell (Bio-Rad). The transfer was completed after 30 min under constant current of 300 mA (Model 200/2.0 Power supply, BioRad). Excess binding sites on the membrane were blocked by incubation of the blots overnight at 4° C. with a blocking solution consisting of 50 mM tris-hydroxy-methyl aminomethane (Tris) HCl, pH 7.5, 150 mM NaCl, 0.05% (v/v) Nonidet-P40, 0.25% (w/v) gelatin and 3% (w/v) BSA. The membrane was washed twice at room temperature with 10 mM Tris-HCl buffer pH 7.5 containing 0.1% Tween-20 and 0.05% (w/v) BSA (TTBS). The membrane was cut into 0.5 cm strips and placed into slots in transfer plates. Mouse anti-EF ascites, Fm16, and normal mouse immunoglobulin G (10.3 mg/ml, Jackson ImmunoResearch Laboratory) were diluted with TTBS (1:500) and added to the respective strips and incubated for an hour at 37° C. in an incubator shaker (model G25 Gyroshaker, New Brunswick Scientific, New Jersey, U.S.A.) set at 100 rpm. The strips were washed three times with TTBS. A goat anti-mouse IgG(H+L)-alkaline phosphatase conjugate (Jackson Laboratories) diluted 1:10, 000 with TTBS was incubated as described above. The strips were washed 3 times with TTBS followed by a final wash with Tris-buffered saline. Antibody binding was visualized by the addition of alkaline phosphatase substrates (nitro blue tetrazolium chloride and 5-bromo-4-chloro-3-indolyl phosphate dissolved in 100 mM Tris-HCl pH 9.5, containing 100 mM NaCl and 5 mM $MgCl_2$). Color development was stopped by rinsing the nitrocellulose strips with deionized water.

EXAMPLE 8

Fungal Cell Agglutination assay

*C. albicans* yeast were cultured in M9 media. The cells were fixed with a 1% (v/v) formalin in PBS pH 7.4 by incubation for 1 h at room temperature. The cells were harvested by centrifugation and washed 3 times with PBS. The cell number was determined in a hemacytometer and adjusted to $2 \times 10^7$ cells/mi. Aliquots (50 µl) were dropped onto microscope glass slides. Aliquots (50 µl) of serially diluted antibodies (Fm16, anti-EF polyclonal antiserum and normal mouse IgG) were added to the *C. albicans* on the slides and incubated for 10 min at 37° C. The agglutination of the yeast were scored by phase contrast microscopy.

EXAMPLE 9

Inhibition of *C. candida* binding to BECs by Mabs.

Whole cell binding assays were carried out as described in Example 4. Antibodies were pre-incubated with the fungal cells, prior to addition to the BEC preparation at the concentrations indicated in FIG. 15.

Antibodies were added to 0.1 mL of yeast in PBS pH 7.2 and incubated for 30 min at room temperature. To this 0.4 mL of PBS pH 7.2 and either 1.0 mL of BECs ($2 \times 10^5$ cells/mL) or 1.0 mL of PBS pH 7.2 was added. The mixture was then incubated at 37° C. shaking at 300 rpm for 2 h. The remainder of the adhesion assay was performed as described in Example 4, above.

EXAMPLE 10

Binding of *Candida albicans* fimbriae to Epithelial Cells

Human buccal epithelial cells (BECs) were collected from 10 healthy, non-smoking male volunteers and washed as described in Example 4.

Both GSLs (asialo-GM$_1$ and CTH) and βGalNAc(1-4)βGal-methylester were used to inhibit *C. albicans fimbriae* binding to BECs. The binding assay was performed using 12 μm polycarbonate filter membranes (Nucleopore Costar Corp.) placed in chambers in a Manifold filtration apparatus equipped with individual vacuum stopcocks (Model FH 225 V, Hoefer Scientific Instruments). The protocols described in Example 4 were employed with the following modifications: *C. albicans* fimbriae (50 μg) were preincubated either βGalNAc(1-4)βGal-methylester, asialo-GM$_1$, or CTH (total volume of 1 ml PBS pH 7.2 containing 0.05% [v/v] Tween-20) at 37° C. for 1 hour. The mixtures were added to BECs (2.0×10$^5$ BECs in 1 ml PBS pH 7.2) and incubated at room temperature for 1.5 hours. The assay mixture consisted of 2.0×10$^5$ BECs, fimbriae (50 μg) and varying concentrations of competitors in a total volume of 1.0 ml of 10 mM phosphate buffer, pH 7.2, containing 150 mM NaCl.

While the invention has been described with reference to specific methods and embodiments, it will be appreciated that various modifications and changes may be made without departing from the invention.

It is claimed:

1. A method of treating an oral or vaginal *Candida albicans* infection in an individual in need of such treatment, comprising
    administering by topical application to the infected site, a pharmaceutically effective amount of a composition of βGalNac(1-4)βGal.

2. The method of claim 1, wherein the composition contains conjugates that are each composed of a carrier structure and multiple βGalNac(1-4)βGal moieties attached to the structure.

3. The method of claim 2, wherein the conjugates are βGalNac(1-4)βGal-polypeptide conjugates in which the polypeptide is the carrier structure, and the βGalNac(1-4)βGal moieties are attached to amino groups on the protein through amide linkages.

4. The method of claim 3, wherein the βGalNac(1-4)βGal moieties have the form βGalNac(1-4)βGal-O(CH$_2$)$_n$CO—, where n=1–10.

5. The method of claim 1, wherein the carrier structure is a polyamine polysaccharide, and the βGalNac(1-4)βGal moieties are attached to carrier structure through amide linkages.

6. The method of claim 5, wherein the βGalNac(1-4)βGal moieties have the form βGalNac(1-4)βGal-O(CH$_2$)$_n$CO—, where n=1–10.

7. The method of claim 2, wherein the conjugates are βGalNac(1-4)βGal-solid-particle conjugates in which the solid particle is the carrier structure.

8. The method of claim 7, wherein the solid particles are particles are silica particles, and the βGalNac(1-4)βGal moieties are linked to the particles through covalent linkages.

* * * * *